US012575732B2

(12) United States Patent
Lee et al.

(10) Patent No.: US 12,575,732 B2
(45) Date of Patent: Mar. 17, 2026

(54) WIRELESS COMMUNICATION SYSTEM FOR WEARABLE MEDICAL SENSORS

(71) Applicant: SIBEL INC., Evanston, IL (US)

(72) Inventors: Jong Yoon Lee, Morton Grove, IL (US); Joo Hee Lee, Morton Grove, IL (US); Ha Uk Chung, Evanston, IL (US); Dennis Ryu, Evanston, IL (US); Shuai Xu, Bala Cynwyd, PA (US)

(73) Assignee: Sibel Inc., Evanston, IL (US)

( * ) Notice: Subject to any disclaimer, the term of this patent is extended or adjusted under 35 U.S.C. 154(b) by 392 days.

(21) Appl. No.: 17/441,992

(22) PCT Filed: Mar. 23, 2020

(86) PCT No.: PCT/US2020/024322
§ 371 (c)(1),
(2) Date: Sep. 22, 2021

(87) PCT Pub. No.: WO2020/198169
PCT Pub. Date: Oct. 1, 2020

(65) Prior Publication Data
US 2022/0167846 A1 Jun. 2, 2022

Related U.S. Application Data

(60) Provisional application No. 62/883,476, filed on Aug. 6, 2019, provisional application No. 62/822,390, filed on Mar. 22, 2019.

(51) Int. Cl.
*A61B 5/00* (2006.01)
*A61B 5/0205* (2006.01)
(Continued)

(52) U.S. Cl.
CPC ............ *A61B 5/0015* (2013.01); *A61B 5/021* (2013.01); *A61B 5/024* (2013.01); *A61B 5/1112* (2013.01);
(Continued)

(58) Field of Classification Search
CPC ....... A61B 5/0015; A61B 5/021; A61B 5/024; A61B 5/1112; A61B 5/14542;
(Continued)

(56) References Cited

U.S. PATENT DOCUMENTS

| | | | |
|---|---|---|---|
| 6,858,006 B2 | 2/2005 | MacCarter et al. | |
| 8,229,535 B2 * | 7/2012 | Mensinger | A61B 5/7445 |
| | | | 600/347 |
| 8,886,334 B2 | 11/2014 | Ghaffari et al. | |
| 9,277,864 B2 * | 3/2016 | Yang | A61B 5/6833 |

(Continued)

FOREIGN PATENT DOCUMENTS

WO 2020198169 A1 10/2020

OTHER PUBLICATIONS

International Search Report and Written Opinion for PCT/US2020/024322 dated Jul. 9, 2020.

*Primary Examiner* — Franklin D Balseca
(74) *Attorney, Agent, or Firm* — Nolte Lackenbach Siegel; N. Alexander Nolte

(57) ABSTRACT
A wireless communication system has a sensor configured to detect a signal indicative of a parameter and generate sensor data as a measurement of the parameter. The sensor has a wireless communication unit configured to wirelessly transmit the sensor data over a network. The wireless communication system also has operational equipment having a central processing unit for processing data and a connection adapter configured to cause the operational equipment to receive the sensor data from the network. The connection adapter comprises a key for enabling the operational equipment to identify the sensor data.

14 Claims, 27 Drawing Sheets

(51) Int. Cl.

| | |
|---|---|
| *A61B 5/021* | (2006.01) |
| *A61B 5/024* | (2006.01) |
| *A61B 5/11* | (2006.01) |
| *A61B 5/145* | (2006.01) |

(52) U.S. Cl.
CPC ........ *A61B 5/14542* (2013.01); *A61B 5/0205* (2013.01); *A61B 2562/08* (2013.01)

(58) Field of Classification Search
CPC ... A61B 5/0205; A61B 5/0002; A61B 5/0004; A61B 5/0006; A61B 5/0008; A61B 5/0011; A61B 5/002; A61B 5/0022; A61B 5/0024; A61B 5/0026; A61B 2562/08; H04Q 9/00; H04Q 2209/00; H04Q 2209/10; H04Q 2209/20; H04Q 2209/25; H04Q 2209/40; H04Q 2209/43; H04Q 2209/47; H04Q 2209/70; H04Q 2209/80; H04Q 2209/82; H04Q 2209/826; H04Q 2209/823; H04Q 2209/84
See application file for complete search history.

(56) References Cited

U.S. PATENT DOCUMENTS

| | | | | |
|---|---|---|---|---|
| 9,396,643 | B2 * | 7/2016 | He | A61B 5/02416 |
| 9,478,148 | B2 | 10/2016 | Ellis | |
| 9,577,455 | B2 * | 2/2017 | Li | G06F 13/4059 |
| 9,585,563 | B2 * | 3/2017 | Mensinger | H04L 67/12 |
| 9,629,574 | B2 * | 4/2017 | Lee | A61B 5/1123 |
| 9,986,314 | B1 * | 5/2018 | Stoddard | A61B 5/02055 |
| 10,470,667 | B2 * | 11/2019 | Corley | A61B 5/1071 |
| 10,854,340 | B2 * | 12/2020 | Harrod, IV | G16H 80/00 |
| 11,271,901 | B2 * | 3/2022 | Gremaud | H04L 63/0272 |
| 11,657,133 | B2 * | 5/2023 | Ackerman | G06F 21/32 |
| | | | | 382/117 |
| 2006/0030765 | A1 | 2/2006 | Swedlow et al. | |
| 2007/0135866 | A1 | 6/2007 | Baker et al. | |
| 2009/0103735 | A1 | 4/2009 | Aizu et al. | |
| 2010/0198032 | A1 | 8/2010 | Simpson et al. | |
| 2010/0234695 | A1 | 9/2010 | Morris | |
| 2013/0282071 | A1 | 10/2013 | Matos | |
| 2015/0312655 | A1 * | 10/2015 | Balakrishnan | G07C 5/0858 |
| | | | | 340/870.07 |

* cited by examiner

Wireless Communication System 5

Wearable Sensor(s) 10

Connection Adapter 20

Operational Equipment 30

Network 40

FIG. 1

WIRELESS COMMUNICATION SYSTEM FOR WEARABLE MEDICAL SENSORS

CROSS REFERENCE TO RELATED APPLICATIONS

This application is a U.S. National Stage filing under 35 U.S.C. § 371 of International PCT Application No. PCT/US20/24322, filed on Mar. 23, 2020, which claims the benefit of priority of U.S. Provisional Patent Application No. 62/822,390, filed on Mar. 22, 2019 and U.S. Provisional Patent Application No. 62/883,476, filed on Aug. 6, 2019, each of which is hereby incorporated by reference in its entirety.

FIELD

The present disclosure relates to a wireless communication system, and, particularly, a wireless communication system for wearable medical sensors.

BACKGROUND

As medical technology progresses, devices such as wearable sensors for on-body physiological and vital sign monitoring have become integral components for effective and efficient patient care and treatment. These systems, however, often depend on individualized (e.g., branded) user interfaces and display monitors for data capture, data display, and data integration with the cloud. In nearly all hospital settings, there are existing monitoring equipment and display units.

Wearable sensors thus often require an additional user interface or device to display data. Therefore, there is a need for the ability for wearable sensors to connect, communicate, and stream data to a wide range of monitoring equipment without the need for an additional display unit. Standard monitoring equipment includes, for example, large display units with multiple input ports for both non-invasive monitoring (e.g., ECG leads, SpO2 cables) and invasive monitoring (e.g. intra-catheter sensors such as arterial lines).

There are challenges, however, to harmoniously connecting and synchronizing the various components, such as wearable medical sensors to monitoring equipment. For instance, the sensors and monitors may be manufactured and produced by different entities and thus lack compatibility on a common platform. Moreover, even if compatible devices are available, it is not a simple matter of upgrading equipment for compatibility, as such equipment is expensive and often remains in use for long part lifetimes.

Accordingly, there is a need for a communication system that can bridge the gap between individual technologies for sensing and monitoring of patient data to enable various components to communicate with each other in a manner that is seamless and easy-to-implement.

SUMMARY

According to exemplary embodiments, the present disclosure describes a wireless communication system. The wireless communication system includes at least one sensor and operational equipment. The sensor is configured to detect a signal indicative of a parameter and generate sensor data as a measurement of the parameter. The sensor includes a wireless communication unit configured to wirelessly transmit the sensor data over a network. The operational equipment includes a central processing unit for processing data. The wireless communication system further includes a connection adapter configured to cause the operational equipment to receive the sensor data from the network. The connection adapter comprises a key for enabling the operational equipment to identify the sensor data.

In some embodiments, the sensor is part of a plurality of sensors each configured to generate sensor data as a measurement of a different parameter. The operational equipment is configured to receive the sensor data associated with the different parameters via the connection adapter and display the sensor data on a monitor.

In some embodiments, the sensor comprises a microcontroller unit and an analog-to-digital converter.

In some embodiments, the operational equipment further comprises at least one output device for displaying the sensor data.

In some embodiments, the operational equipment comprises a patient monitor.

In some embodiments, the operational equipment comprises a port for receiving the connection adapter, the port having a custom pin receiving configuration, and wherein the key comprises wired output unit in the form of a pin insert configuration configured to mate with the port pin receiving configuration.

In some embodiments, the connection adapter further comprises a port configured with the same custom pin receiving configuration as the operational equipment port.

In some embodiments, the connection adapter comprises a wireless communication unit configured to connect to the network.

In some embodiments, the connection adapter is connected to the operational equipment through a local area network.

In some embodiments, the connection adapter is a Bluetooth receiver.

In some embodiments, the system includes a plurality of connection adapters each configured to receive the sensor data over the network and forward the sensor data to the operational equipment through the local area network.

In some embodiments, the sensor transmits the sensor data to the connection adapter based on signal strength detected from the plurality of connection adapters.

In some embodiments, the connection adapter is an embedded data receiver integrally formed with the operational equipment.

In some embodiments, the connection adapter is a virtual adapter formed as software installed on the central processing unit.

In some embodiments, the network is a wireless wide-area network.

In some embodiments, the operational equipment is a remote processor configured to receive the sensor data and the key is an electronic signature transmitted with the sensor data for identifying the sensor data.

In some embodiments, the connection adapter comprises at least one wireless communication unit and is configured to connect to the operational equipment over a wireless wide area network.

In some embodiments, the connection adapter comprises a plurality of wireless communication units, including a first wireless communication unit configured to connect to the sensor via the network and a second wireless communication unit configured to connect to the operational equipment via the wireless wide-area network.

In some embodiments, the network is a local network and the wireless wide area network is a cellular data network.

In some embodiments, the connection adapter is a charging station configured to provide electrical charge to a gateway and receive the sensor data through the network.

In some embodiments, the gateway is the sensor.

In some embodiments, the gateway is connected to a plurality of sensors that comprises the sensor.

In some embodiments, the charging station includes a near field communication device configured to receive the key from the sensor and provide the key to the operational equipment for authentication.

In some embodiments, the connection adapter is configured to communicate with the sensor and the operational equipment bi-directionally.

In some embodiments, the connection adapter is configured to receive sensor control instructions from the operational equipment and deliver the sensor control instructions to the sensor through the network.

In some embodiments, the connection adapter is connected to the operational equipment through a wireless wide-area network.

In some embodiments, the sensor control instructions comprise a triggered alarm as a result of an event detected by one or more of the connection adapter or operational equipment.

In some embodiments, the operational equipment comprises a remote processor and a computing device, the remote processor is configured to trigger an alarm as a result of an event detected based on the sensor data received by the network and send the alarm to the computing device by a wireless wide-area network, and the wireless wide-area network is different than the network.

In some embodiments, the sensor is a wearable sensor and the parameter is a vital sign.

In some embodiments, the sensor is flexible and/or stretchable.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the inventions described herein, there is shown in the drawings embodiments that are presently preferred, it being understood, however, that the inventions are not limited to the specific instrumentalities disclosed. Included in the drawings are the following Figures:

FIG. 1 is a block diagram of an exemplary wireless communication system;

DETAILED DESCRIPTION OF EXEMPLARY EMBODIMENTS

Figure 2:
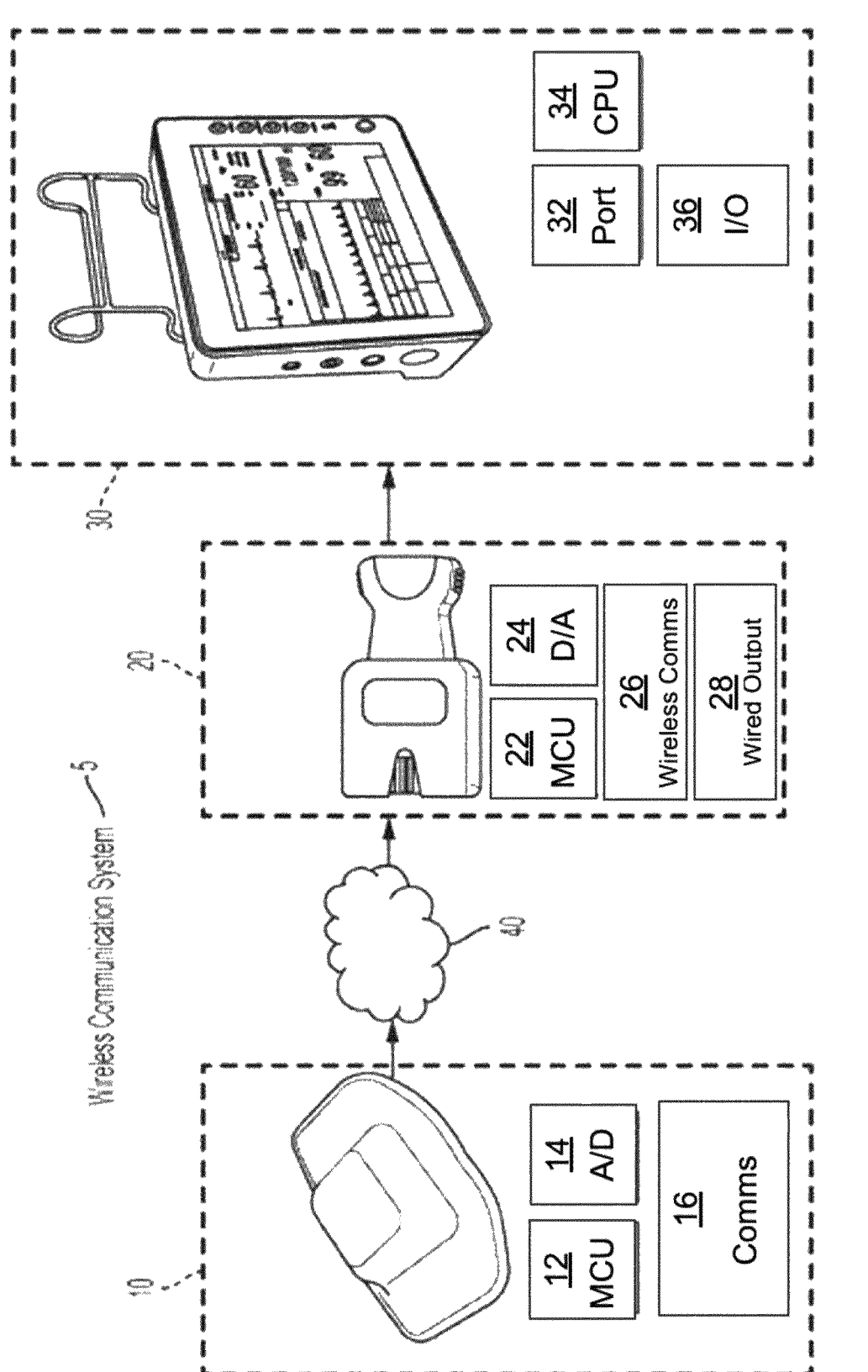
FIG. 2 is a diagram of the wireless communication system, according to an embodiment.

The following disclosure describes a wireless communication system and constituent components configured to enable wireless communication between separate devices in a medical monitoring and patient care environment. Embodiments are applicable, for example, to a system including one or more sensors configured to collect data through monitoring of a parameter, such as ECG data, accelerometer data, gyroscope data, temperature, pulse oximetry, pulse arrival time, pressure, etc. The disclosed embodiments provide adaptive components configured to deliver such data to operational equipment, such as monitoring equipment with display output, data processing, and alarm monitoring functionality based on received data. In an exemplary embodiment, disclosed systems may include hardware configured to convert the operational equipment from a device capable of receiving data through wired, plug-in connections to devices with wireless receipt and transmission capabilities for communicating with the wireless sensors in the system. In other embodiments, disclosed systems may include hardware to deliver sensor data to a remote processor through a Wireless Wide-Area Network (WWAN).

Figure 1:
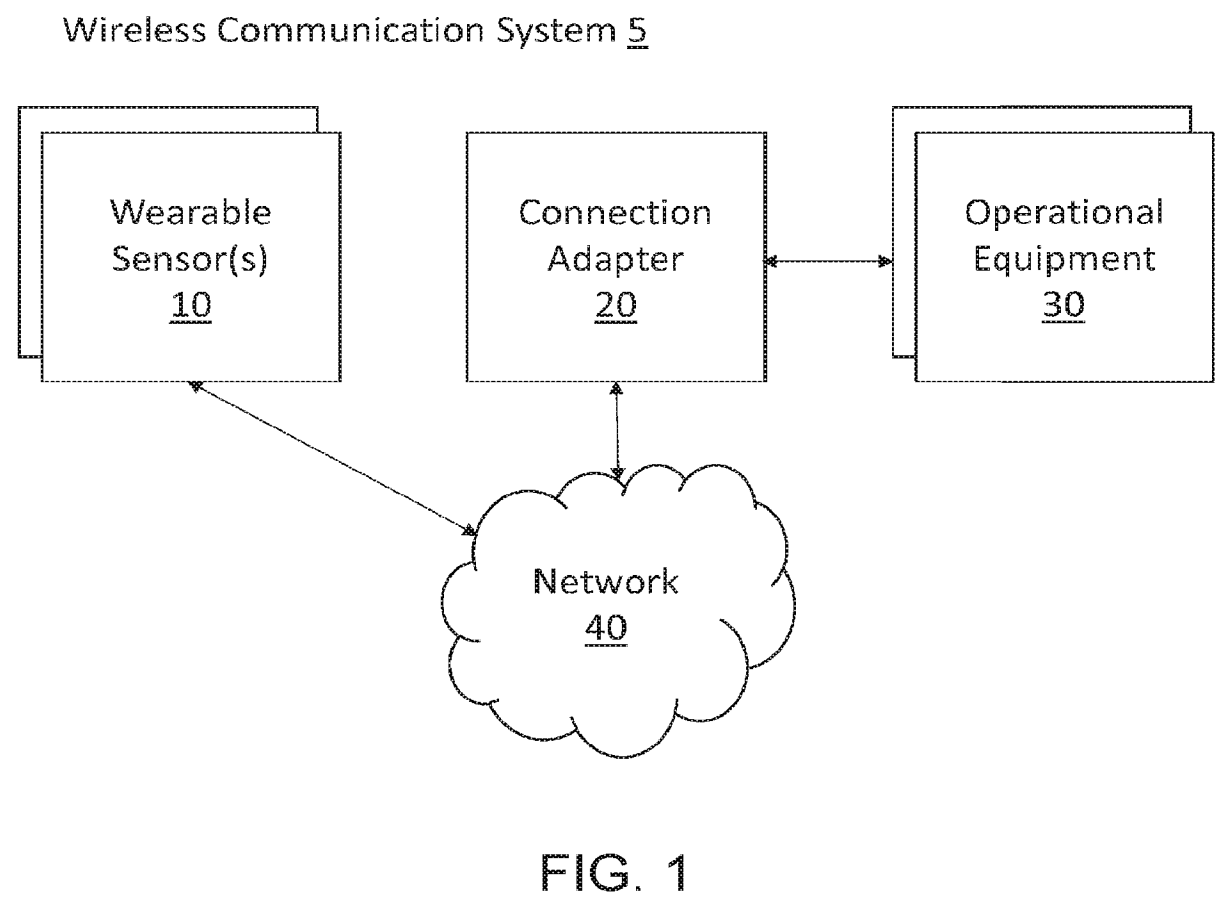

FIG. 1 is a block diagram of a wireless communication system 5 for implementation in a medical data collection and patient monitoring environment. The wireless communication system 5 may include, for example, one or more sensors 10, at least one connection adapter 20, operational equipment 30, and a network 40. The wireless communication system 5 may be in a form of the various embodiments described herein but is not limited to only those depicted embodiments and can include other systems having the components shown, including systems having additional or alternative components other than those shown in FIG. 1.

The sensor(s) 10 may be a medical sensing device configured to produce a signal indicative of a parameter, such as a patient vital sign. In some embodiments, the sensor(s) 10 are wearable medical sensors configured to directly adhere to the human body. The sensor(s) 10 may be flexible and/or stretchable to further promote ease of wearing by a user. U.S. Pat. Nos. 9,277,864 and 8,886,334, which are herein incorporated by reference in their entirety, describe examples of wearable sensors capable of wireless communication. The sensor(s) 10 are configured detect a plurality of physiological measurements (e.g. electrical, pressure, chemical, impedance, resistance, temperature, movement) and produce a signal indicative of the associated parameter. In an exemplary embodiment, the sensor 10 is configured to detect an analog signal and convert the signal into a digital domain, although embodiments are not limited to such sensors. The sensor(s) 10 may include various components, such as on-board computing for signal processing to derive vital signals (Heart Rate, Respiratory Rate, SpO2, Blood Pressure, Core body temperature) and/or filtering of the physiological data on the sensor 10 itself. The sensor may be further configured to package the digital signal in various ways that include, but are not limited to, compression of data, downsample of the data, and encryption of the data. The sensor 10 may be configured to provide packaged data to the wireless network 40.

The connection adapter 20 may be a hardware and/or software component configured to provide the operational equipment 30 with wireless capabilities. For instance, the connection adapter 20 may be configured to receive the data collected by the sensor 10. In some embodiments, the connection adapter 20 provides wireless capabilities to operational equipment that otherwise does not have wireless communication ability. In some embodiments, the connection adapter 20 is a separate, plug-in component configured to interface with an existing external or internal port of the operational equipment 30. In other embodiments, the connection adapter 20 may be an integrated internal component installed in the operational equipment 30. In still other embodiments, the connection adapter 20 may be a virtual component configured to bridge a connection between wireless-capable devices that do not otherwise know how to connect and/or communicate with each other.

In at least some embodiments, the connection adapter 20 is configured to provide a key to the operational equipment that allows the operational equipment to identify sensor data from the sensor 10. The key may include, for example, a particular hardware pin insert configuration that fits into a particular port in the operational equipment. The hardware pin insert may be a self-authenticating key. The key may be a software key that authenticates the sensor 10 and acts as a digital signature to enable the operational equipment to identify the data stream from the sensor 10.

The operational equipment 30 may be one or more medical monitoring devices configured to collect patient data and perform one or more operations to use the data for patient care. For instance, the operational equipment 30 may be a vital sign monitor configured to output pulse and ECG information for observation by a user. In other embodiments, the operational equipment may be a remote processor configured to collect patient data from one or more sensors 10 over time and perform operations on such data, such as processing and/or delivery to other components.

The network 40 may be a wireless network configured to facilitate communication between the components of the system 5, including, for example, wireless communication between the sensor(s) 10 and the connection adapter 20. The network 40 may be implemented in one or more forms, including, for example, Bluetooth®, Zigbee, Bluetooth Mesh, Thread, ANT, 802.15.4, Wi-Fi, Local Area Network (LAN), Near Field Communication (NFC), and other known communication protocol. In some embodiments described herein, the network 40 may be a WWAN, such as a 5G or LTE cellular data network.

FIG. 2 is a diagram of the wireless communication system 5, including a sensor 10 as a wearable sensor, a connection adapter 20 as a separate connection dongle configured to directly connect to a port of a piece of operational equipment 30. The sensor 10 is configured to wirelessly communicate with the connection adapter 20 via the network 40, which, for example, may be a Bluetooth connection. The sensor 10 may include constituent components, such as a microcontroller unit (MCU) 12 which may be Arm Cortex based, an analog-to-digital (A/D) converter 14, and a communications unit 16. The MCU 12 may include a processor and, in some instances, an on-board memory for performing functions such as signal processing, classification of an event, data storage, data filtering, data packaging, and/or event detection functionality. For instance, the MCU 12 may be configured to execute software instructions stored in a memory to perform one or more processes or steps of processes described herein.

The A/D converter 14 is configured to convert an analog signal detected by the sensor 10 into a digital signal for transmission by the communications unit 16. In some embodiments, the A/D converter 14 may optionally also include a digital-to-analog converter (D/A), such as to revert a received digital signal to an analog domain for feedback control.

The communications unit 16 may be, for example, a transmitter for providing packaged data to the network 40 for wireless transmission. In some embodiments, the communications unit 16 may be a transceiver to additionally enable the sensor 10 to receive data, such as data from the network 40. The communications unit 16 may be configured to communicate with the MCU 12 to determine data packets to forward to the network 40. Such data packets may include measured parameters of the sensor 10 or authentication data for pairing the sensor 10 to another device (e.g., the connection adapter 20).

The connection adapter 20, according to an embodiment, includes an MCU 22, a digital-to-analog (D/A) converter 24, a wireless communications unit 26, and a wired output unit 28. The MCU 22 may include a processor and memory for signal processing and data reconstruction, for example. The D/A converter 24 is configured to convert a digital signal received at the wireless communications unit 26 into an analog signal. The wired output 28 may be a customized pin arrangement for plug-in compatibility with an existing port of operational equipment 30. For instance, the wired output 28 may include a particular pin-insert configuration for a port of a vital sign monitoring device that would typically receive a connection wire of a hard-wired sensor having that pin-insert configuration. In this way, the connection adapter 20 may be configured to take the place of a wired connection without the operational equipment 30 being modified or detecting that a wireless connection is in use. The wired output 28 thus is a key to enable the operational equipment 30 to identify the data stream received through the connection adapter 20.

The operational equipment 30 may include various components depending on the device configuration. In an exemplary embodiment, the operational equipment 30 includes a port 32 configured to mate with the wired output unit 28 of the connection adapter 20. The operational equipment 30 may additionally include a central processing unit (CPU) 34, and one or more I/O devices 36, such as a digital display.

The operational equipment 30 is configured to receive data from the connection adapter 20 at the port 32. The received data may have been wirelessly transmitted from the sensor 10 to the connection adapter 20 and delivered to the operational equipment 30 for analysis and/or output to a user. The CPU 34 is configured to perform data processing in a manner the same as or similar to processing that would occur if the data had been received through a hard-wired connection to the port 32. The connection adapter 20 may be configured such that the operational equipment cannot discern between data received wirelessly or from a wired connection, as the wired output 28 is preferably configured to match the otherwise wired output to which the operational equipment may be designed to connect (e.g., through the customized pin insert arrangement of the wired output unit 28).

Port 32 may have a configuration that includes but is not limited to RS232 ports, PS/2, LAN, USB, etc.). Operational equipment 30 that may be configured to connect to connection adapter 20 to produce wireless communication capabilities may be monitoring and other devices from common manufacturers that include but are not limited to: General Electric, Philips, Siemens, Draeger, SpaceLabs and Mindray and include all medical monitoring modules of this type.

The wired output 28, according to at least some embodiments, is a self-authenticating key in that its physical connection to the operational equipment 30 is sufficient for the operational equipment 30 to identify the data stream received via the connection adapter 20. For instance, the operational equipment 30 does not require additional hardware or software to determine the source of the data stream, as the operational equipment 30 is configured to treat the data wirelessly received at the connection adapter 20 as if it was being received through a wired device, such as an ECG lead on a wire. In some embodiments, the connection adapter 20 may itself be configured to perform authentication (e.g., Bluetooth pairing, NFC communication, QR code scanning, etc.).

Figure 3:
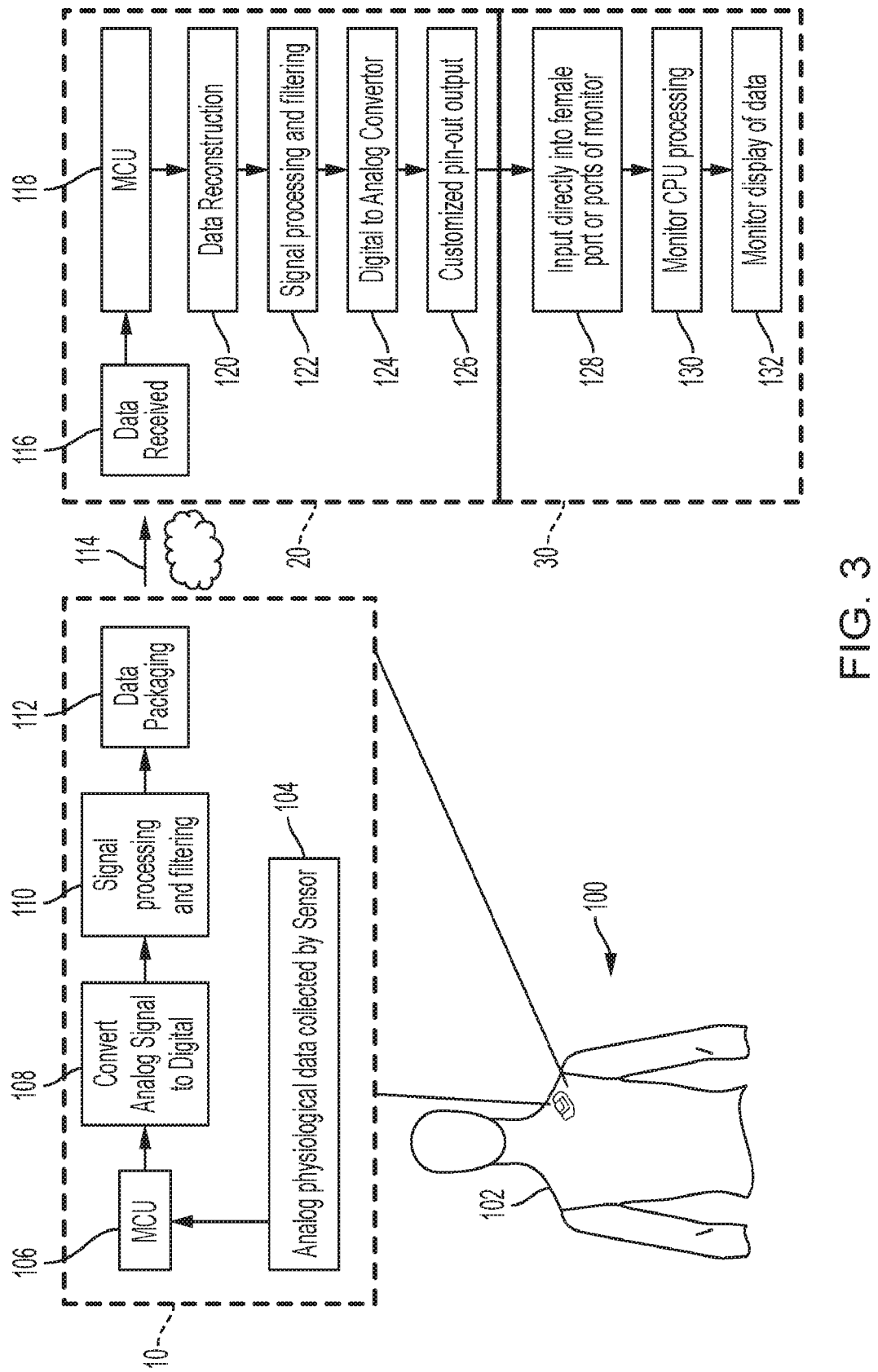
FIG. 3 is a flowchart of an exemplary process for wirelessly transmitting sensor data to operational equipment.

FIG. 3 is a flowchart of an exemplary process 100 for delivering data to operational equipment 30 from the sensor 10 based on a signal monitored and output by the sensor 10 and wirelessly transmitted to the connection adapter 20. At step 102, the wearable sensor 10 is positioned for use, such by placement on a human body. At step 104, analog data (e.g., physiological data) is collected by the sensor 10. At step 106, the MCU 12 receives the analog data and at step 108, the A/D converter 14 converts the processed analog signal into a digital signal. At step 110 the MCU 12 processes and filters the data according to processing functions stored in a memory connected to the MCU 12. At step 112 the MCU 12 packages the converted signal for transmission. At step 114, the communications unit 16 provides the packaged data to the network 40 for wireless transmission, where it is received by the wireless communications unit 16 of the connection adapter 20 at step 116.

The received data at the connection adapter is forwarded to the MCU 22 of the connection adapter 20 at step 118, where it is reconstructed at step 120 and processed and filtered at step 122. In step 124, the D/A converter 24 converts the processed signal back from a digital domain to an analog domain and provides the analog signal to the wired output 28 at step 126. At step 128, the connection adapter 120 delivers the signal to the operational equipment 30 through the wired output 28 where it is received at the port 32. At step 130, the CPU 34 of the operational equipment processes the received signal. At step 132, the operational equipment may output the received data to a user, such as through display of the data at display (e.g., I/O device 36).

Figure 4:
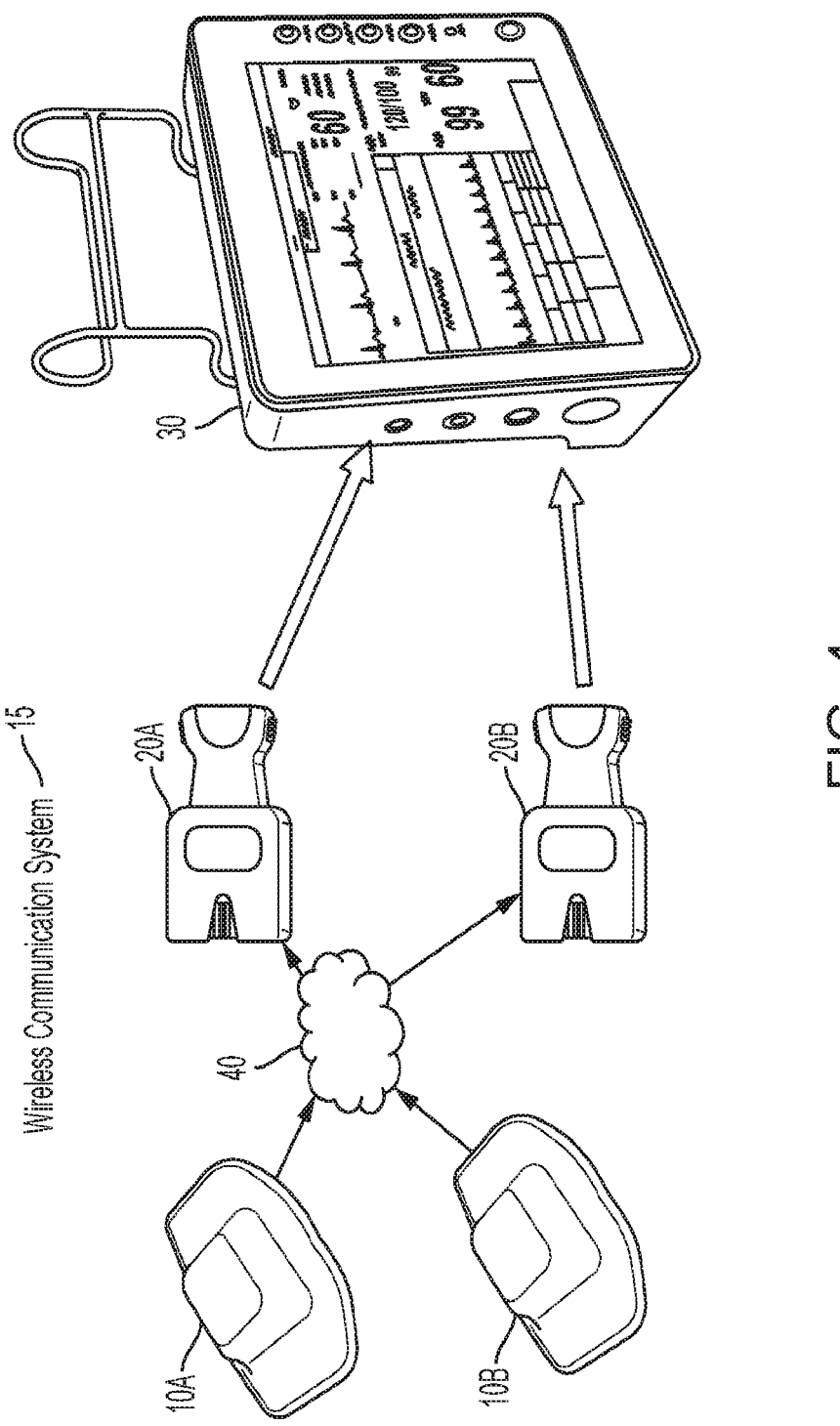
FIG. 4 is a diagram of the wireless communication system, according to an embodiment having multiple sensors.
Figure 5:
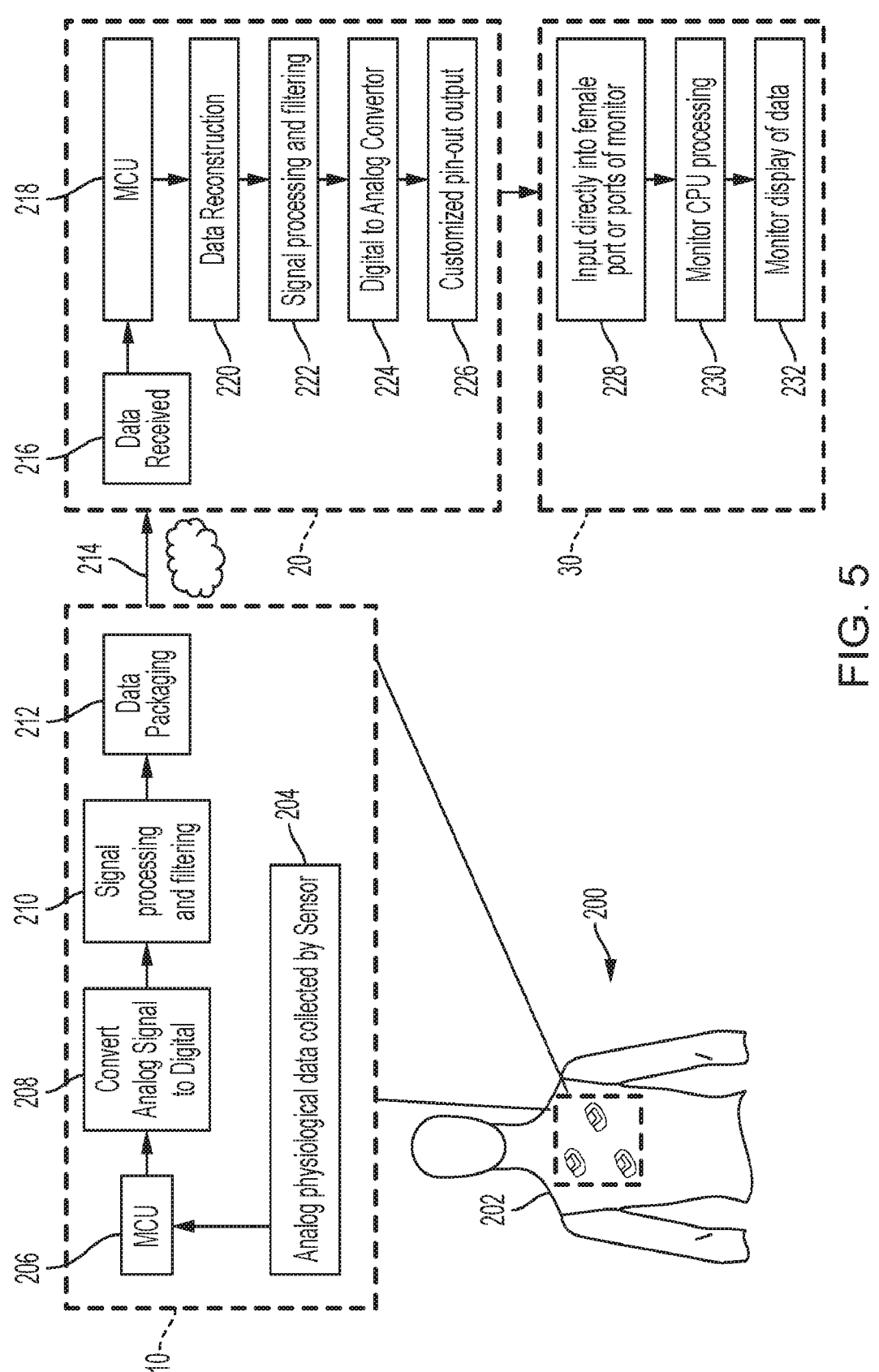
FIG. 5 is a flowchart of an exemplary process for wirelessly transmitting sensor data from multiple sensors to operational equipment.

FIG. 4 is a diagram of an embodiment of a wireless communication system 15 having a plurality of sensors 10A, 10B configured to provide monitored data to the network 40 for delivery to one or more connection adapters 20A, 20B configured to connect to operational equipment 30. For instance, sensors 10A, 10B may be configured to detect different medical parameters, such as pulse and ECG, that may typically be collected through a wired connection to the operational equipment 30 (e.g., a monitoring device for displaying patient vital signs). The sensors 10A, 10B may be individually capable of wireless transmission of collected data to the connection adapters 20A, 20B. The connection adapters 20A, 20B may be similarly configured to the connection adapter 20 of FIG. 2. The connection adapters 20A, 20B may include different wired output units 28 such as for connecting to different ports 32 of the operational equipment 30. For instance, connection adapter 20A may include a wired output unit 28 with a first pin-insert configuration (e.g., associated with a pulse oximeter) and the connection adapter 20B may include a wired output unit 28 with a second pin-insert configuration (e.g., associated with a thermometer). In other embodiments, the connection adapters 20A, 20B may be a singular component configured to deliver the separate data streams from the sensors 10A, 10B to one or more ports of the operational equipment 30. The sensors 10A, 10B, connection adapters 20A, 20B, and operational equipment 30 may otherwise include the components shown and described in relation to FIG. 2 for performing one or more process, such as the process 200 shown in FIG. 5. The process 200 may include steps 202-232 that correspond to steps 102-132 for wireless delivery of data to the operational equipment 30, repeated in parallel for the multiple sensors 10A, 10B, and/or multiple connection adapters 20A, 20B. In some embodiments, a plurality of sensors 10 may be formed in a single device and may package different measured parameters for communication via the network 40.

Figure 6:
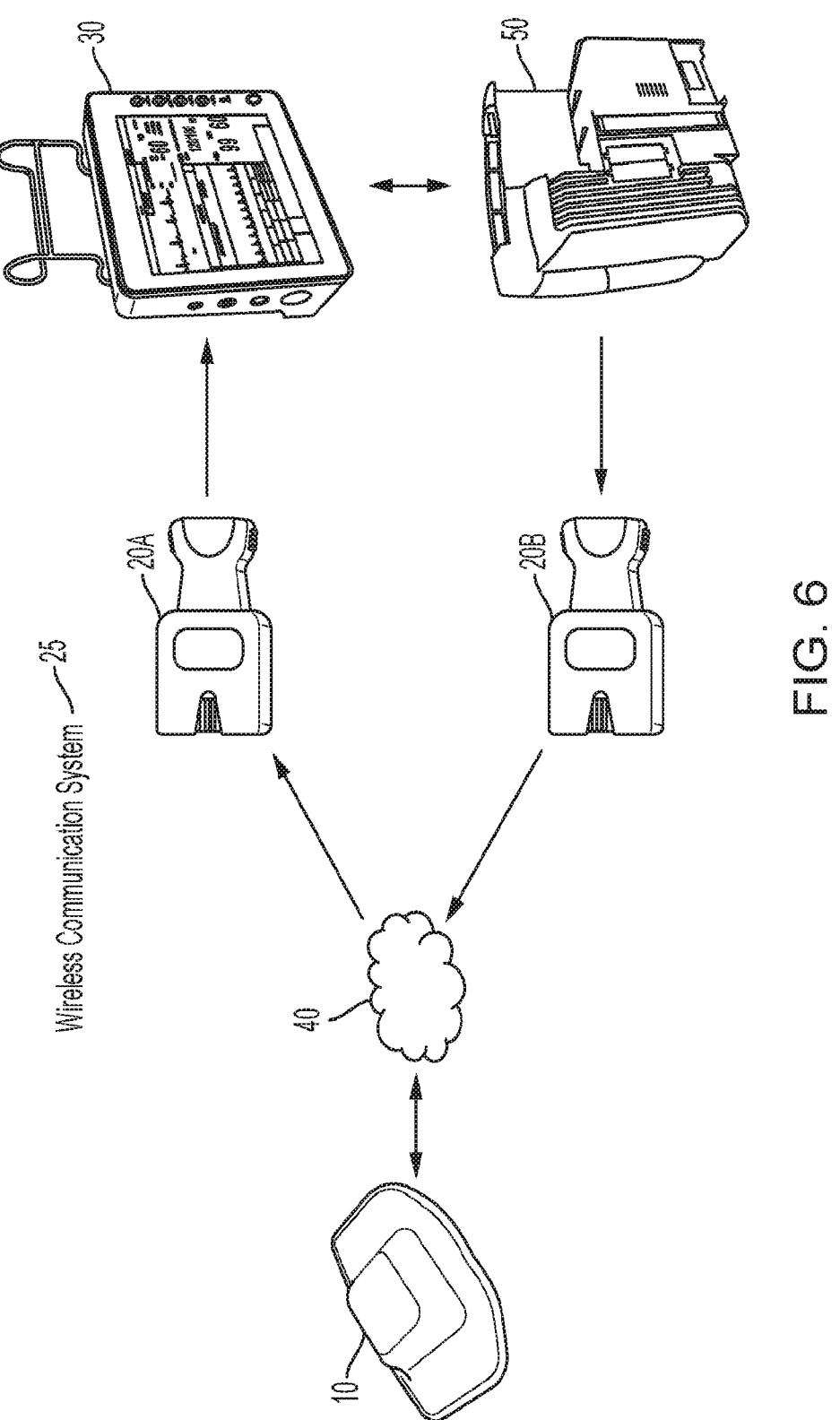
FIG. 6 is a diagram of the wireless communication system, according to an embodiment having a feedback system for returning data to the sensor.

FIG. 6 is a diagram of an embodiment of a wireless communication system 25 that includes bidirectional feedback from a sensor 10 and operational equipment 30, such as a standard medical monitor. In this embodiment, the sensor 10 transmits data to the connection adapter 20A that is then plugged directly into the operational equipment 30. The connection adapter 20A may be further configured (e.g., through a transceiver function or through a separate connection adapter 20B) to receive data from the operational equipment 30 (or a separate alarming system 50) and perform transmission of data back to the sensor 10 such as to trigger an alarm on the sensor 10. This alarm can then trigger an action on the sensor 10 which includes activation of a visual (light emitting diode), acoustic (sound), tactile (vibratory motor) to notify patients and/or providers.

Figure 7:
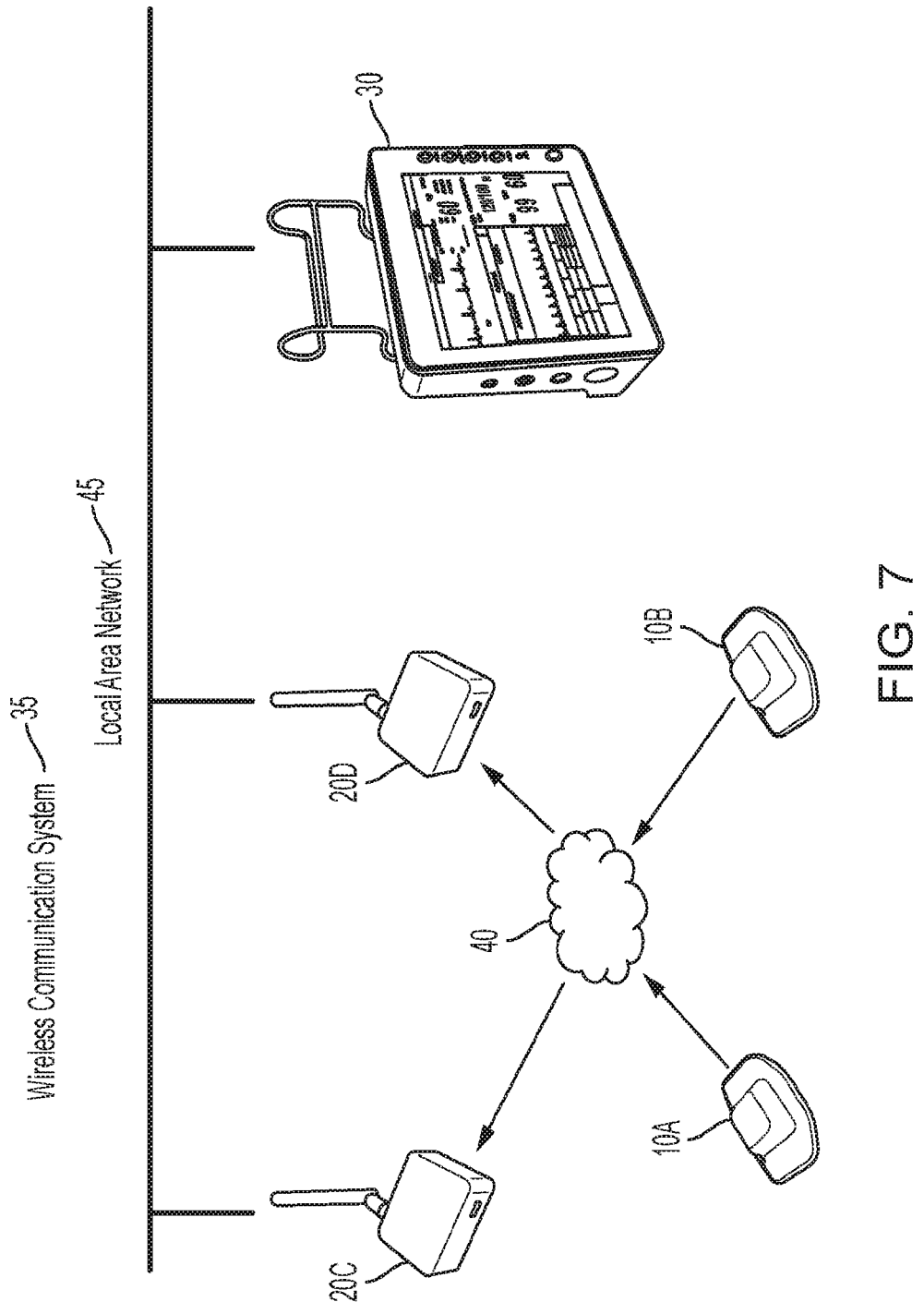
FIG. 7 is a diagram of the wireless communications system, according to an embodiment using a local area network to collect sensor data from one or more sensors.

FIG. 7 is a diagram of an embodiment of a wireless communication system 35 that includes connection adapters 20C, 20D in the form of wireless receivers connected to the network 40 and a local area network (LAN) 45. For instance, the connection adapters 20C, 20D may be Bluetooth receivers configured to receive wireless signals from the sensors 10A, 10B via the network 40 (e.g., Bluetooth communication protocol). The system 35 further includes operational equipment 30 in the form of a monitor that is connected to the LAN 45.

In some embodiments of the system 35, the sensors 10A, 10B are configured to emit a wireless signal and connect to connection adapter 20C, 20D with the highest signal strength (RSSI). The sensors 10A, 10B transmit data to the connection adapters 20C, 20D which may then enter the LAN 45. The LAN may utilize communication standards that include but are not limited to ISO/IEEE 11073. Operational equipment 30 that are compatible with the communication standard will receive the data to be displayed via the LAN 45. The sensors 10A, 10B are thus configured to jump between different connection adapters (e.g., Bluetooth receivers) as the signal strength changes, thereby allowing continuous monitoring as the patient changes location. The system 35 may allow multiple sensors 10A, 10B connected to different connection adapters 20C, 20D in some embodiments that require extra bandwidth between the sensor and adapter for high sampled/resolution data.

Figure 8:
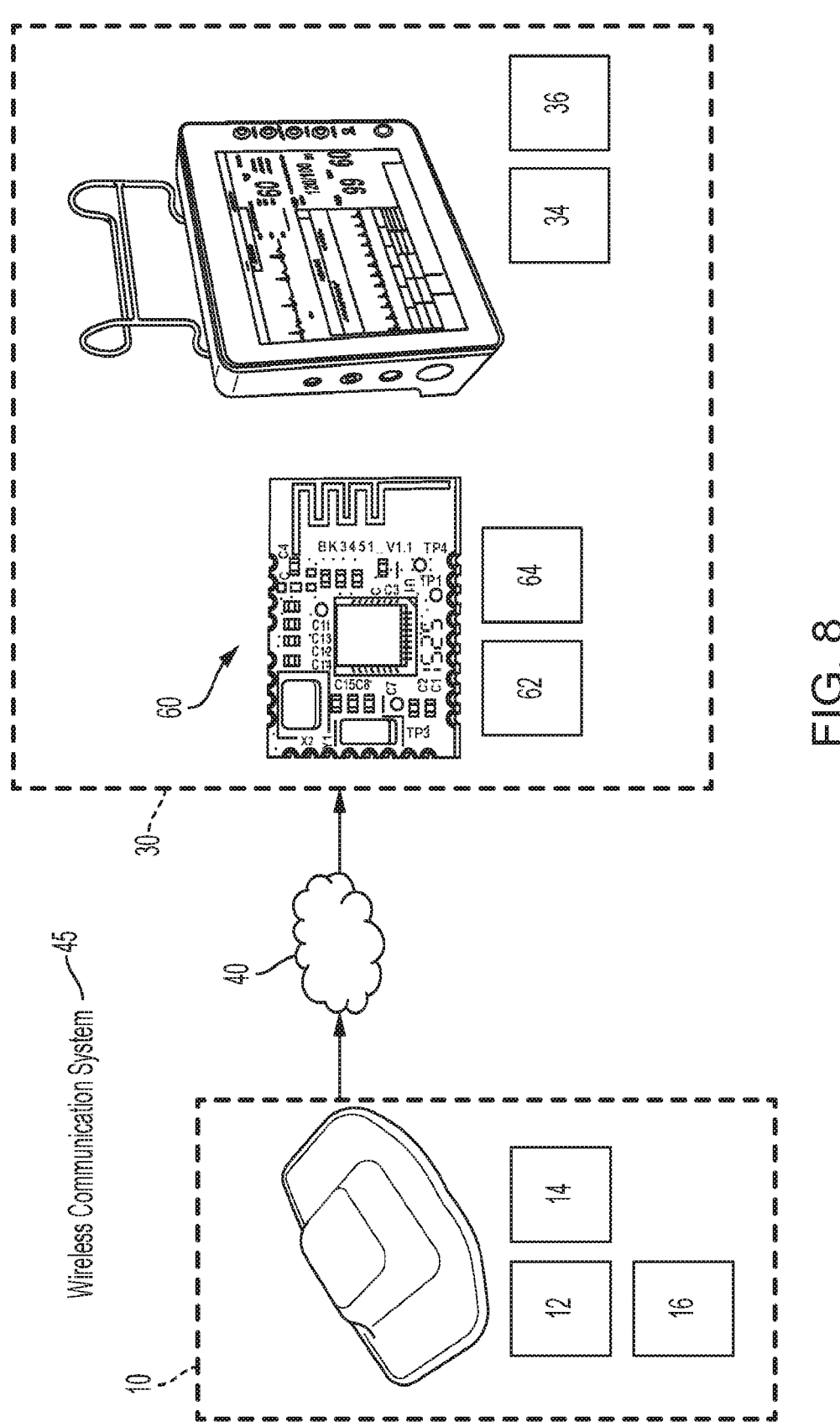
FIG. 8 is a diagram of the wireless communications system, according to an embodiment having an communication device integrally formed with operational equipment.

FIG. 8 is a diagram of an embodiment of a wireless communication system 45 in which the connection adapter 20 is an embedded data receiver 60 integrally formed into the operational equipment 30. The embedded data receiver 60 may be hardwired into operational equipment 30 that otherwise is with or without onboard wireless capabilities. The sensor 10 may include the components 12, 14, 16 (e.g., MCU, A/D converter, communications unit) for receiving, processing, filtering, packaging, and providing data to the network 40 for wireless transmission. The operational equipment 30 may include CPU 34 and I/O 36 for receipt, processing, and display of received data. The embedded data receiver 60 may include at least a wireless communications unit 62 and an MCU 64 for receiving and processing data from the network 40. The embedded data receiver 60 is configured as a built-in component for delivery of received data to the CPU 34 for display by a display (e.g., I/O device 36).

In some embodiments, the embedded data receiver 60 may be a standard wireless receiver built-in to operational equipment 30. For instance, more advanced monitoring systems may be manufactured with Bluetooth or Wi-Fi capabilities. In some embodiments, a connection adapter 20 may be a virtual component in the form of a software installation that teaches the embedded data receiver 60 to communicate with a wireless sensor 10. For example, the connection adapter 20 may be downloaded from an external drive or a wired or wireless Internet connection. For instance, the connection adapter may include a virtual key in place of the custom pin-insert configuration in order to match a particular sensor 10 to operational equipment 30.

Figure 9:
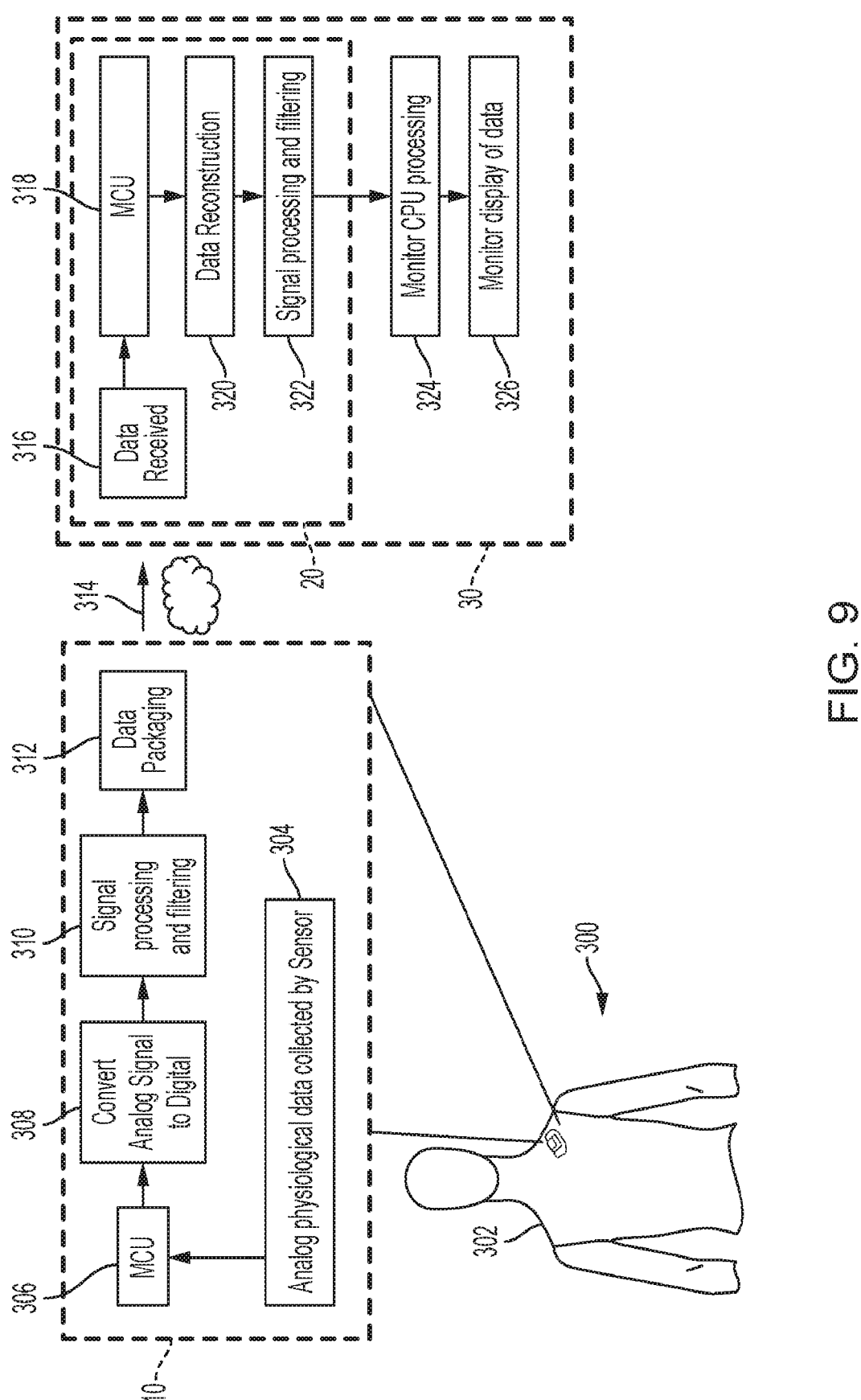
FIG. 9 is a flowchart of an exemplary process for wirelessly transmitting data to operational equipment having the integrated communication device.

FIG. 9 is a flowchart of a process 300 for sensor data processing in the communications system 45. The process 300 may include in step 302 a sensor 10 being positioned for detecting a signal indicative of a parameter, such as a vital sign through attachment to a patient. The sensor 10 may be a flexible, wearable sensor with data collection, processing, and wireless communication capabilities, such as through the similar description accompanying FIG. 2.

In step 304, the sensor 10 detects analog data, such as the vital sign of the patient. At step 306, the MCU 12 receives the analog data. At step 308, the A/D converter 14 converts the processed analog signal into a digital signal. At step 310 the MCU 12 processes and filters the data according to processing functions stored in a memory connected to the MCU 12. At step 312 the MCU 12 packages the converted signal for transmission. At step 314, the communications unit 16 provides the packaged data to the network 40 for wireless transmission, where it is received by the wireless communications unit 62 of the embedded data receiver 60 at step 316. The embedded data receiver 60 may receive the sensor data at the MCU 64 at step 318. The MCU 64 may perform data reconstruction in step 320 and signal processing and filtering at step 322. The embedded data receiver 60, being an integrated component of the operational equipment 30 may forward the processed data to the CPU 34 for processing in step 324 and onto the I/O 36 for display at step 326.

Figure 10:
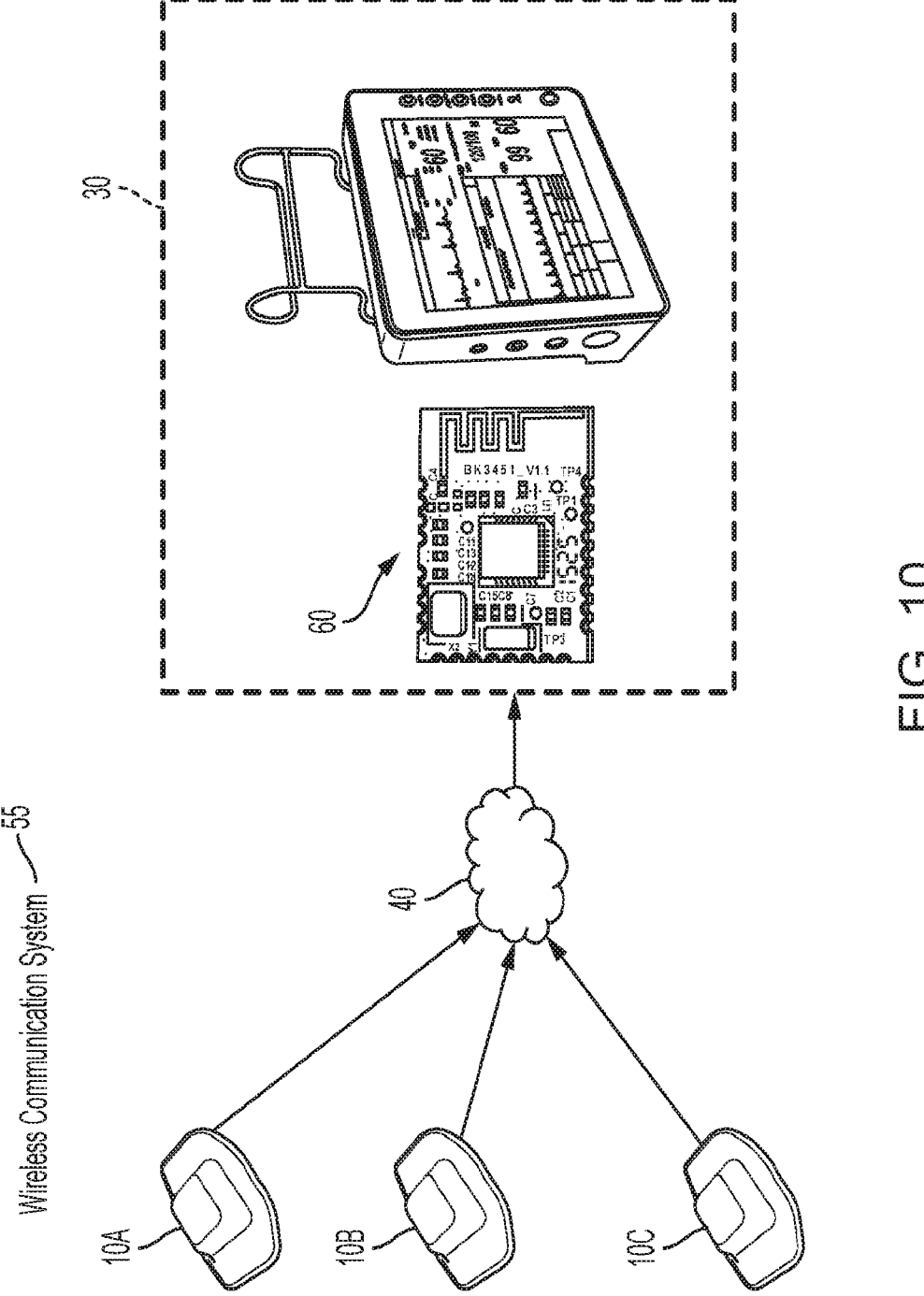
FIG. 10 is a diagram of the wireless communication system, according to an embodiment having multiple sensors and the integrated communication device.
Figure 11:
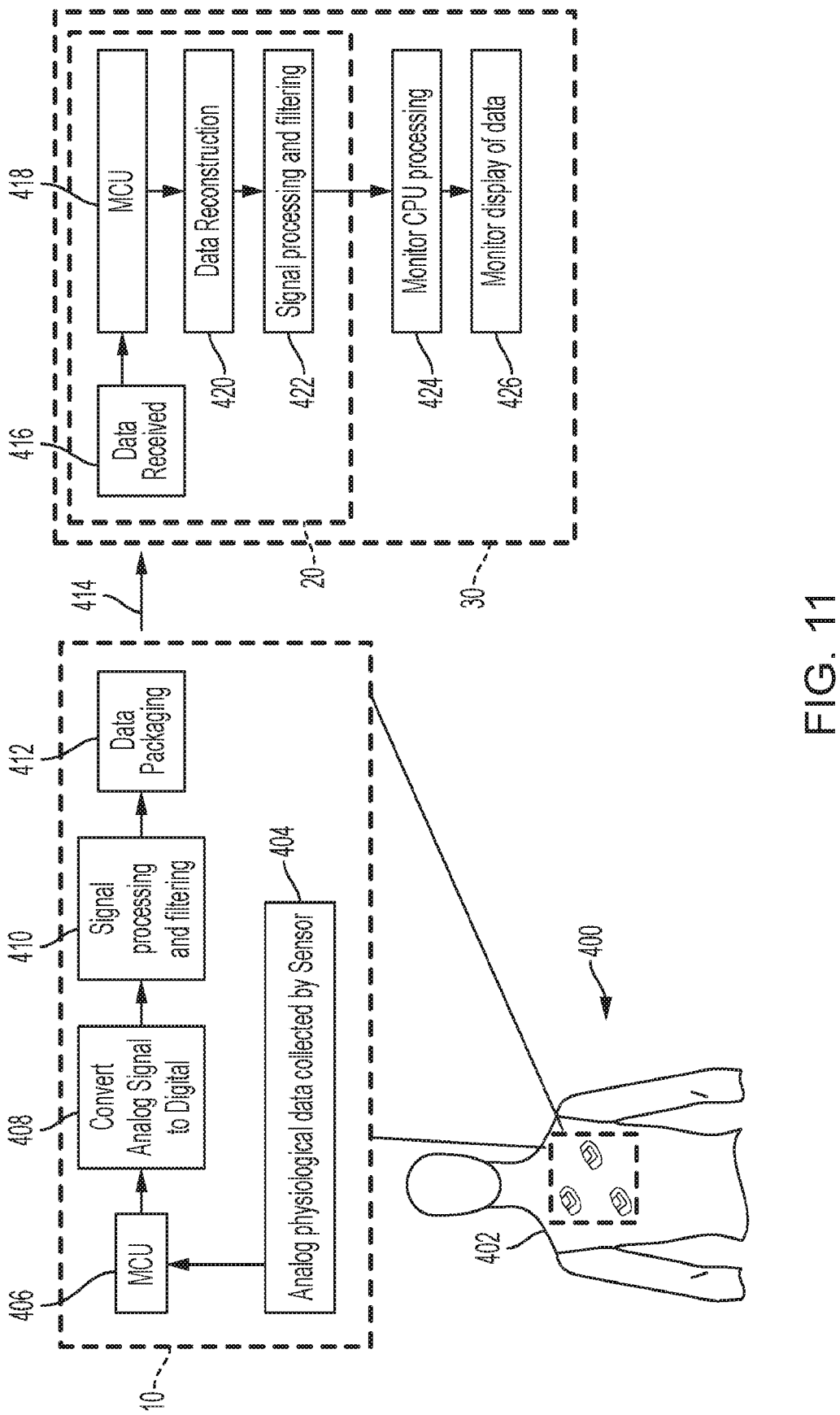
FIG. 11 is a flowchart of an exemplary process for wirelessly transmitting data from multiple sensors to operational equipment having the integrated communication device.

FIGS. 10-11 are a diagram and flowchart, respectively, showing how multiple sensors 10A, 10B, and 10C are configured to send signals to the embedded data receiver 60. FIG. 10 includes a wireless communication system 55 having the multiple sensors 10A, 10B, and 10C. Each sensor 10A, 10B, 10C may be configured to communicate with the network 40 wirelessly to provide a sensor data stream that is collected at the embedded data receiver 60 and displayed by the operational equipment 30. A process 400 of FIG. 11 corresponds to the process 300 of FIG. 9 and includes steps for delivering sensor data from multiple sensors to the operational equipment 30. Process 400 includes steps 402-426 corresponding to steps 302-326 of process 300.

Figure 12:
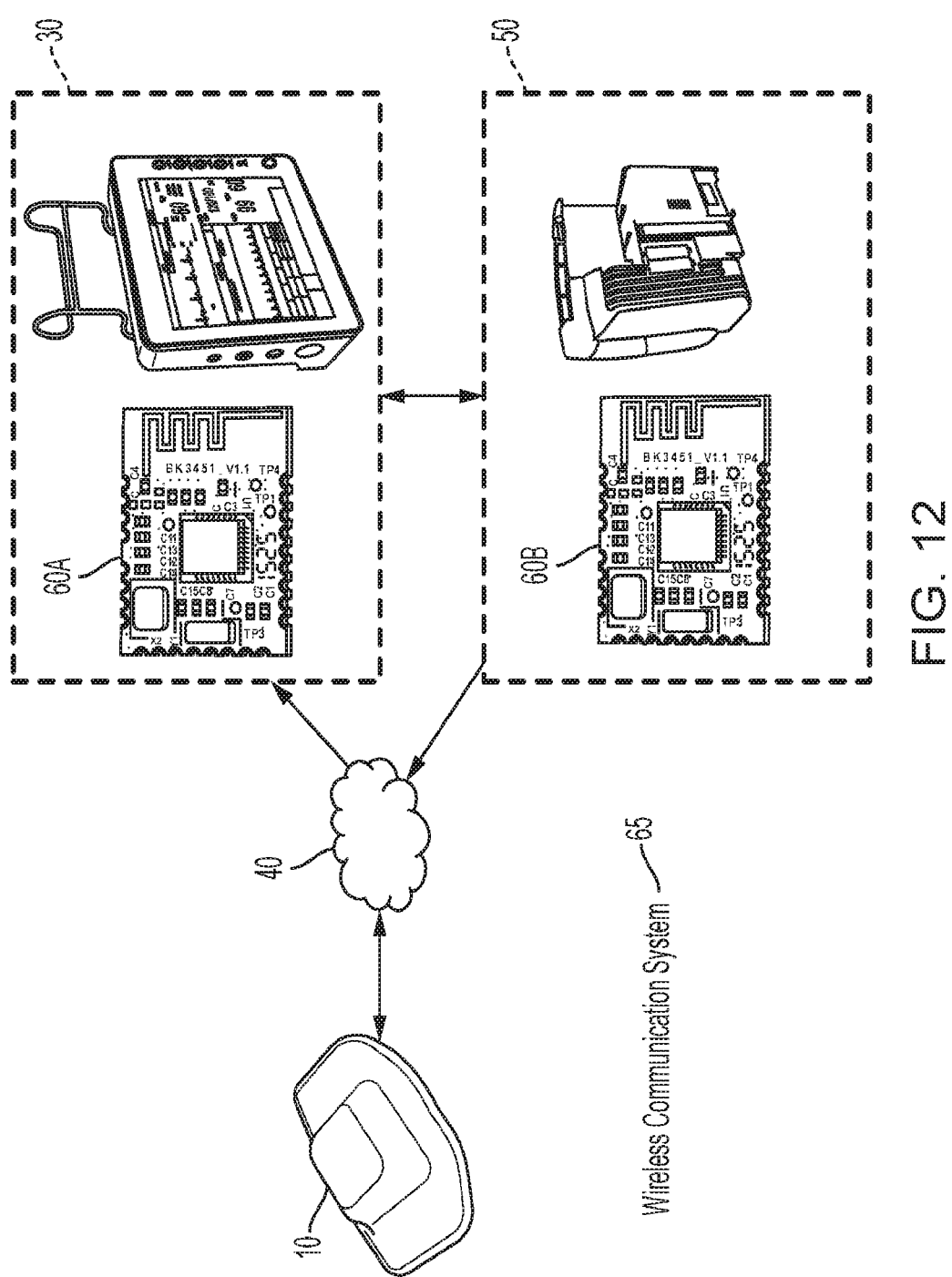
FIG. 12 is a diagram of the wireless communication system, according to an embodiment having a feedback system for returning data to the sensor and one or more integrated communication devices.

FIG. 12 is a diagram of a wireless communication system 65 in which an embedded data receiver 60A can both accept and transmit data to and from the sensor 10 triggering sensor actions (visual, sound, or haptic notification) through feedback control. The embedded data receiver 60A may perform both receipt and transmission of data (e.g., through a transceiver) or a separate alarming device 50 may include a separate embedded data receiver 60B for analyzing monitored data and providing feedback to the sensor 10 through the network 40.

Figure 13:
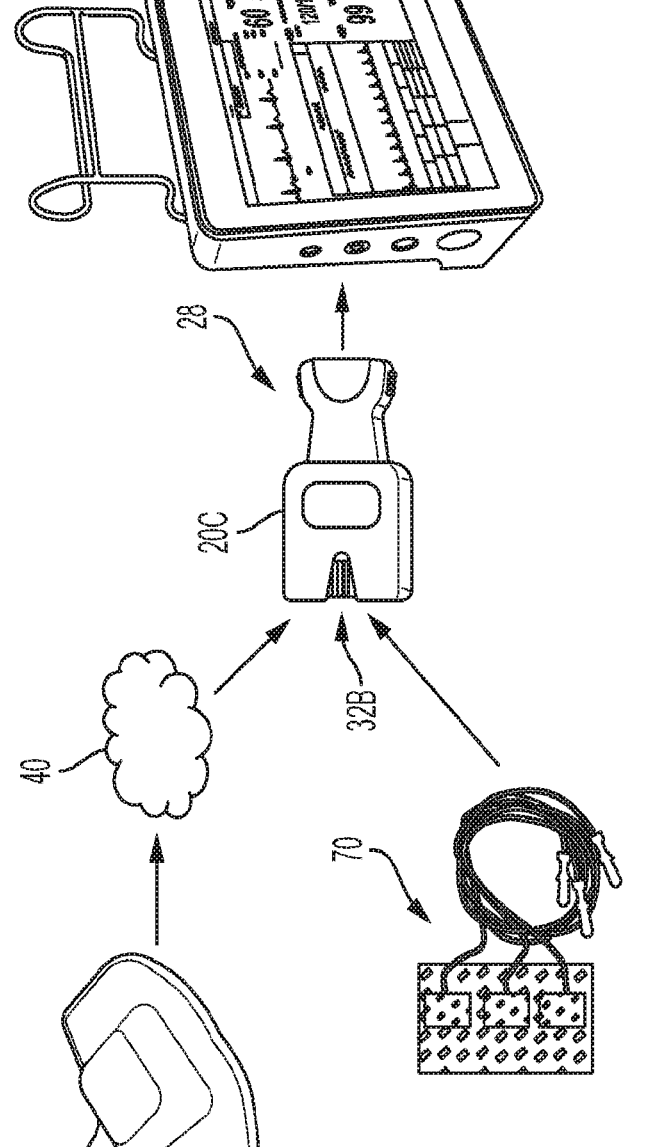
FIG. 13 is a diagram of the wireless communication system, according to an embodiment having wireless and wired input into a connection adapter.

FIG. 13 illustrates an embodiment of a wireless communications system 75 that includes a connection adapter 20C configured to accept both wireless signals from a sensor 10 as well as accept wired inputs from traditional accessories 70. For instance, the connection adapter 20C may include an additional female port that passively transmits data directly to the operational equipment 30. For instance, the connection adapter 20C may include a wired output unit 28 that matches a customized pin-insert configuration of the port 32 of the operational equipment 30 and the connection adapter 20C may further include a port 32B that accepts the same pin-insert configuration of the wired output unit 28 such that the connection adapter 20C may act as a pass-through and does not close the port 32. This embodiment may be used in instances where wireless communication fails or a secondary monitoring modality is required (e.g. in instances of cardiac defibrillation). The connection adapter 20C may also broadcast data as a transmission unit to other mobile devices in some embodiments.

Figure 14:
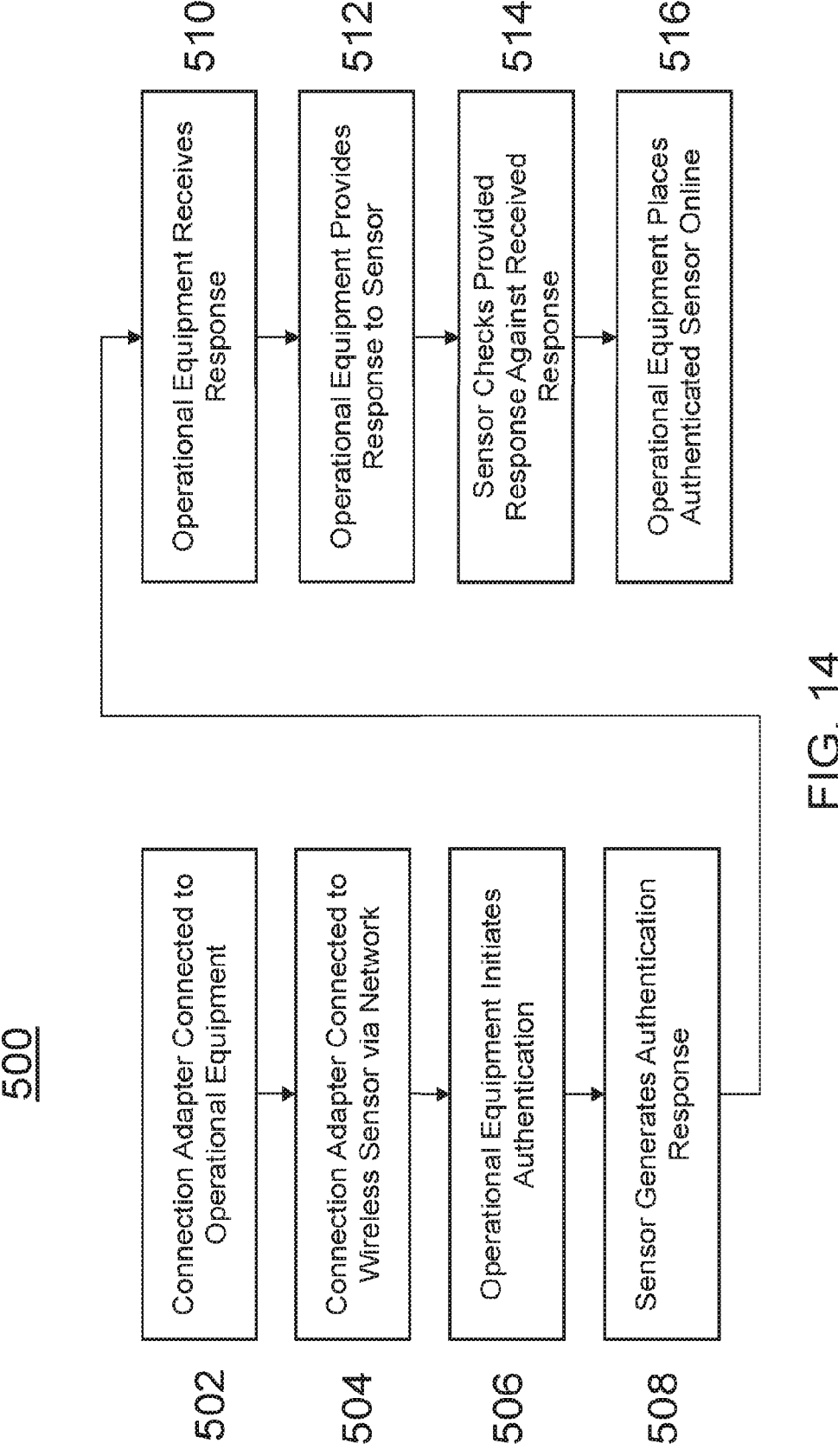
FIG. 14 is a flowchart of an exemplary process for connecting a sensor to operational equipment through a connection adapter and authenticating the sensor with the operational equipment.

FIG. 14 is a flowchart of an exemplary process 500 for connecting a sensor 10 to operational equipment 30 for wireless transmission and receipt of monitored sensor data (e.g., patient vital signs or other medical data). One or more components of the disclosed wireless communication systems may perform one or more steps of the process 500. For example, the sensor 10, connection adapter 20, and/or operational equipment 30 may perform one or more steps of the process 500 through computer-implementation (e.g., via MCU, CPU, processor, memory, etc.).

In step 502, the connection adapter 20 is connected to the operational equipment 30. In one example, the external connection adapter 20 is plugged into a port 32 of the operational equipment 30. In another example, an embedded data receiver 60 is the connection adapter and is built-in to the operational equipment 30 (e.g., during manufacturing). In still other embodiments, the connection adapter 20 is a virtual component connected to the operational equipment 30 through software execution that enables wireless communication with a particular sensor 10. In some embodiments (e.g., as shown in FIG. 7), the connection adapter 20 is connected to the operational equipment by a LAN 45.

In step 504, the connection adapter 20 is connected to the wireless sensor 10 via the network 40. For example, the connection adapter 20 may be paired to the sensor 10 through a Bluetooth connection. In another example the connection adapter 20 and the sensor 10 may be connected via Wi-Fi. In still another embodiment, the network 40 may be a WWAN and the connection adapter 20 and sensor 10 may have cellular communication components.

In step 506, the operational equipment 30 initiates an authentication of the sensor 10. In at least some instances, the authentication of the sensor 10 enables the operational equipment 30 to classify and/or identify the data stream from the sensor 10. For instance, the operational equipment 30 may be in a room with several sensors 10 and may receive multiple wireless transmission via the connection adapter 20. The authentication process may act as a virtual signature to enable the operational equipment 30 to understand and separate the various received data streams. The authentication may include sending an authentication request to the sensor 10. In step 508, the sensor 10 generates a response to the authentication request. In some embodiments, the response by the sensor 10 may be a key or ID that enables the operational equipment 30 to identify the sensor 10, and,/or the sensor 10 to identify the operational equipment 30.

In step 510, the operational equipment 30 receives the response from the sensor 10. The operational equipment 30 may receive the authentication response through an I/O device 36, such as a manual or automated input device. In one example, a user inputs the sensor response. In another example, a component of the operational equipment automatically detects the sensor response. In step 512, the operational equipment 30 provides the received sensor response back to the sensor 10. For instance, the operational equipment may send a wireless signal through the same path (e.g., network 40) as the authentication request in step 506. In step 514, the sensor 10 checks the response received from the operational equipment 30 with the original generated response. If the responses match, the sensor 10 communicates with the operational equipment 30 and the operational equipment 30 places the sensor 10 online in step 516. If the responses do not match, the sensor is not placed online and/or an error is output by the sensor 10 and/or operational equipment 30.

The process 500 may provide the operational equipment 30 with an ability to determine how to interpret data signals that are received by the connection adapter 20. In a wired connection, the operational equipment 30 would not likely receive multiple data streams at the associated port 32. However, the connection adapter 20 may create a situation in which multiple data streams from similar sensors 10 are sent to the operational equipment 30. For instance, a patient monitor may be in the same room as multiple patients wearing similar sensors. The authentication process with process 500 enables the operational equipment to securely pair with a sensor 10 and output the correct data for displaying to a user. It should be understood, however, that in some embodiments authentication may be completed at the network 40, such as through Bluetooth pairing or restricted Wi-Fi configurations.

Figure 15:
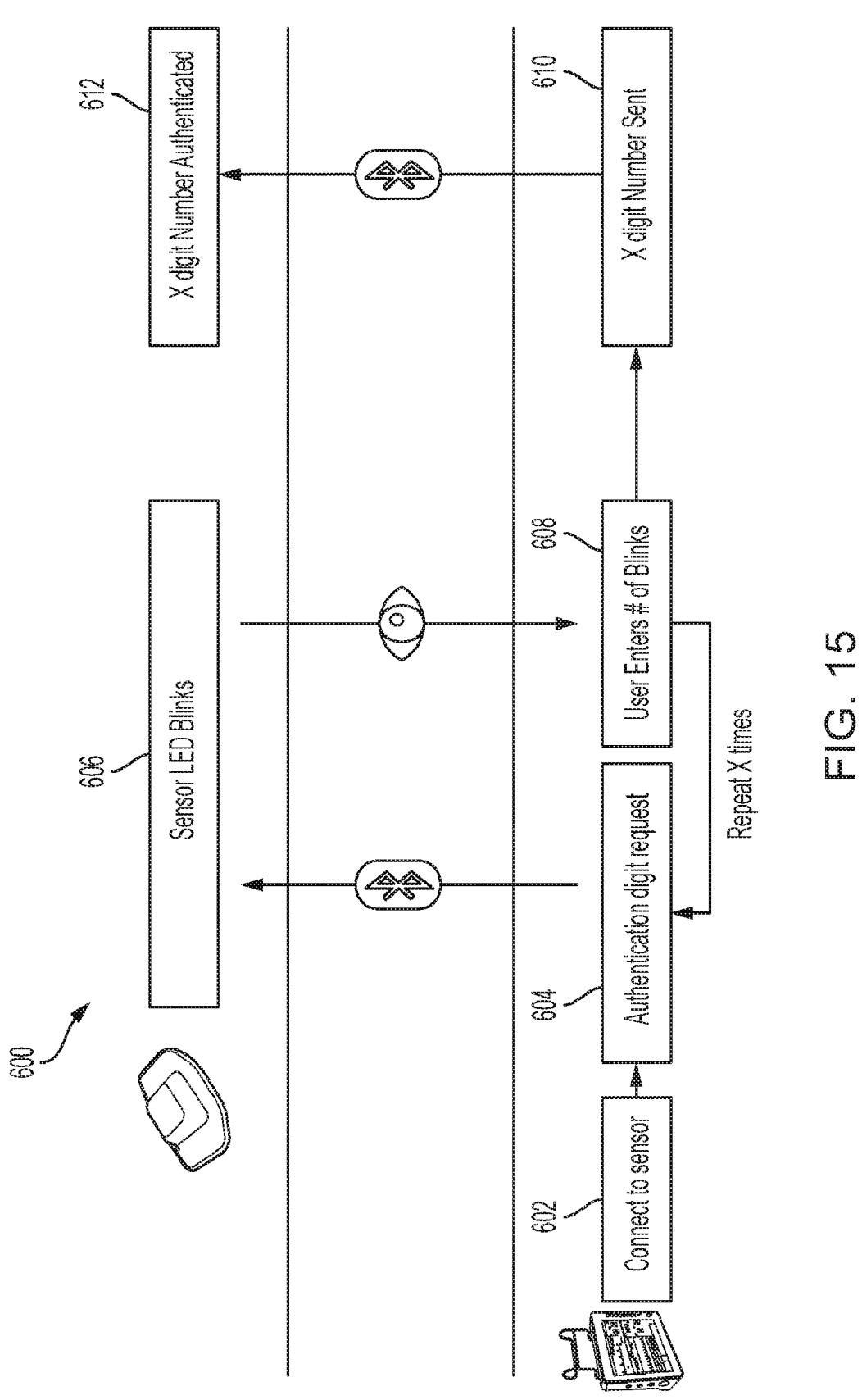
FIG. 15 is a flowchart of the process for authenticating a sensor with operational equipment, according to an embodiment.
Figure 16:
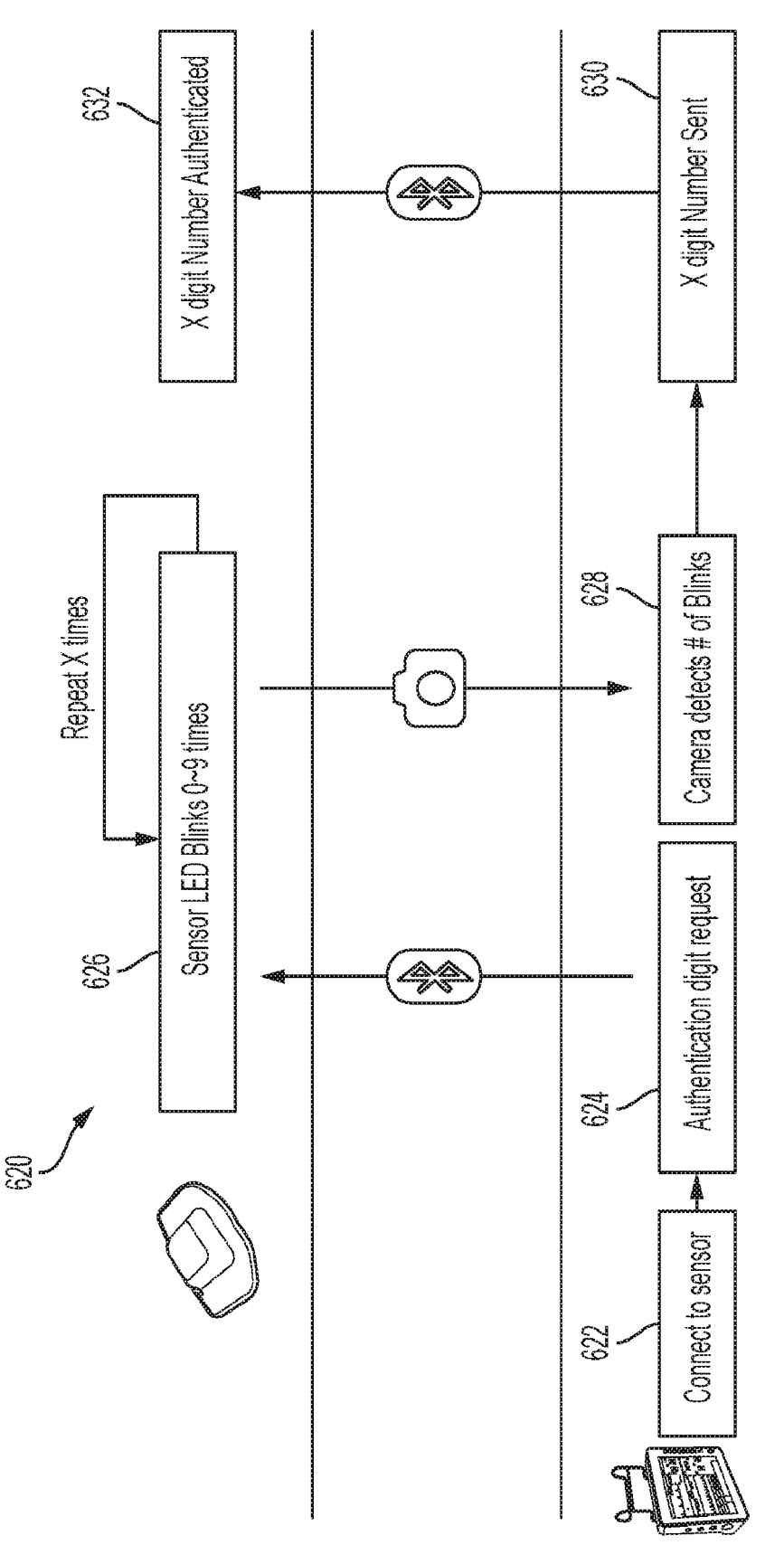
FIG. 16 is a flowchart of a process for authenticating a sensor with operational equipment, according to another embodiment.

FIG. 15 is a flowchart of a process 600 that includes an exemplary authentication embodiment. This embodiment allows the sensors 10 to be authenticated using a single LED on the sensor 10. At step 602, the operational equipment 30 connects to the sensor 10 through the connection adapter 20. The operational equipment 30 sends an authentication request to the sensor 10 at step 604. The authentication request includes a digit request that tells the sensor 10 to blink at step 606. A user manually counts a number of blinks on the sensor 10 and enters it on an input display as a passcode (e.g., a 6-digit passcode through repeated digit entering) at step 608. At step 610, the entered passcode is sent back to the sensor 10. The sensor 10 checks the passcode against the original generated digits and thereby authenticates the sensor 10 at step 612. FIG. 16 describes another embodiment that allows LED authentication with a camera as an I/O device 36 on the operational equipment 30. The LED blinking is automatically counted and compared to the original passcode for authentication. In still other embodiments, the camera may be configured to scan a QR code on the sensor 10 to authenticate and pair the sensor 10.

Figure 17:
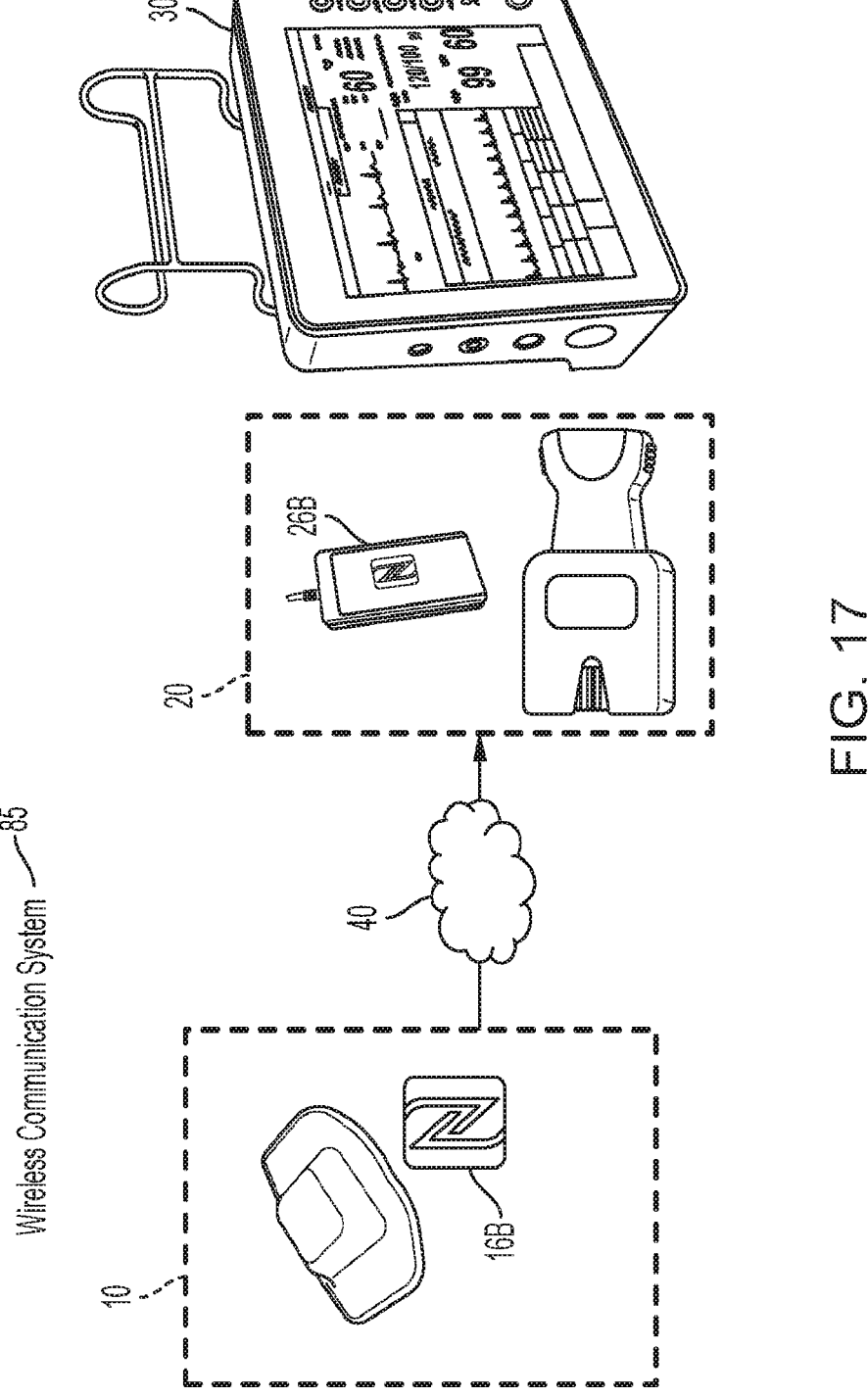
FIG. 17 is a diagram of the wireless communication system, according to an embodiment having Near-Field-Communication components for authentication of a sensor.

FIG. 17 is a diagram of a wireless communication system 85 that uses near field communication (NFC) for sensor authentication. The sensor 10 includes a wireless communication unit 16B in the form of an NFC device. The NFC device is used for pairing with the operational equipment 30. For instance, an NFC reader 26B embedded in the connection adapter 20 may be used to authenticate the sensor 10 by placing the sensor 10 in range of the detector.

Figure 18:
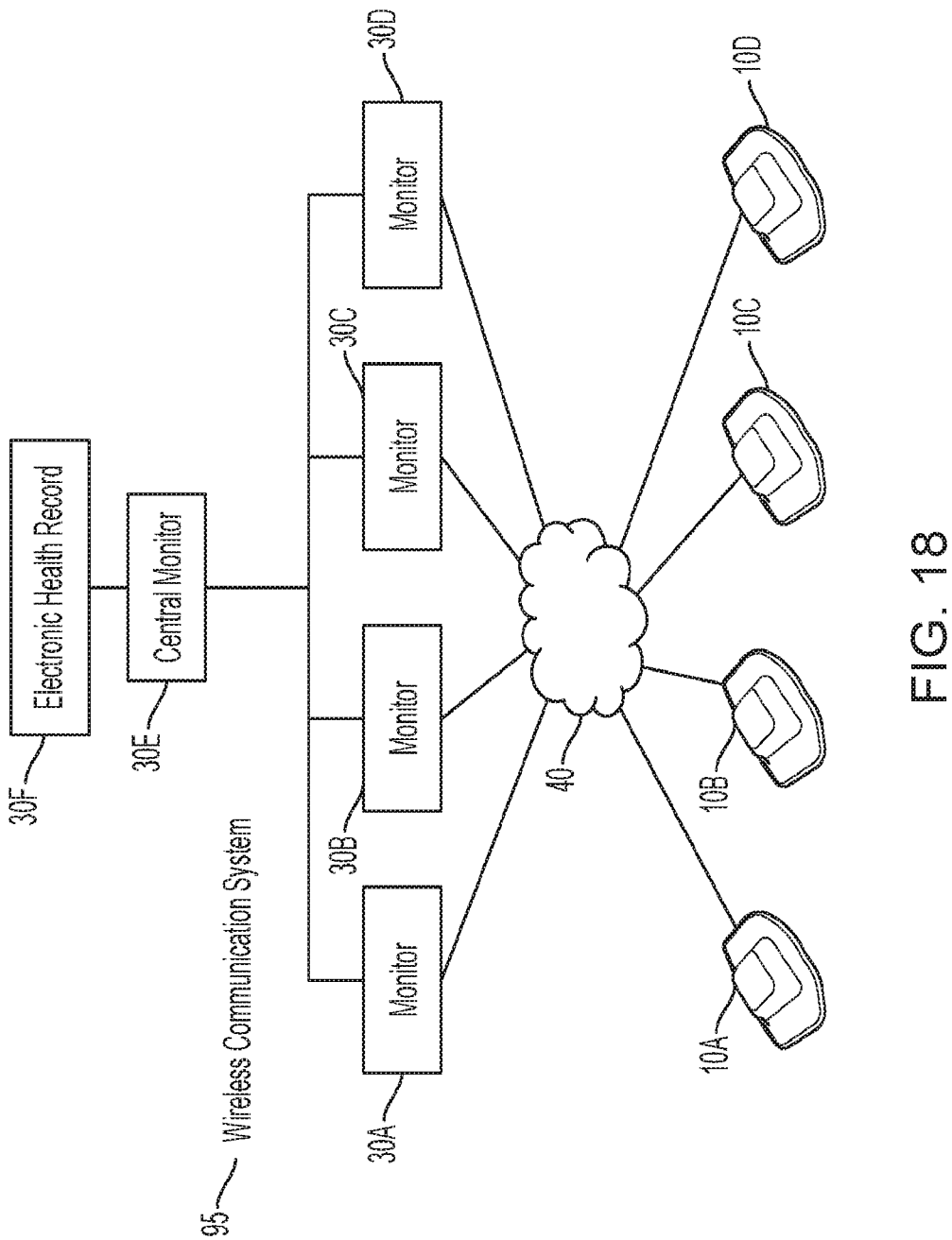
FIG. 18 is a diagram of the wireless communication system, according to an embodiment having multiple operational equipment devices each connected to separate sensors.

FIG. 18 is a diagram of a wireless communication system 95 in which a plurality of sensors 10A, 10B, 10C, 10D separately communicate with a plurality of operational equipment 30A, 30B, 30C, 30D in the form of separate patient monitors. For instance, four patients may each have vital sign monitors that receive wireless sensor data. In system 95, the monitors 30A-D further communicate with a central patient monitor 30E, thereby enabling a user to supervise multiple patients at once. The central monitor 30E may communicate, for example, via the network 40 with the monitors 30A-D. In other embodiments, the central monitor 30E is connected to the patient monitors 30A-D through wired connections. The central monitor 30E may then transfer data to an electronic health record 30F, such as to update a patient medical record in real-time.

The sensor 10, as described herein, may be a flexible, wearable sensor with processing capability. For example, signal processing, filtering, and event detection may occur on the sensor 10 itself. In below described embodiments, data collected from the body or events detected are then transmitted wirelessly via a WWAN. Various embodiments support a plurality of WWAN network types (e.g. LTE-M, 5G, LoRaWAN).

Figure 19:
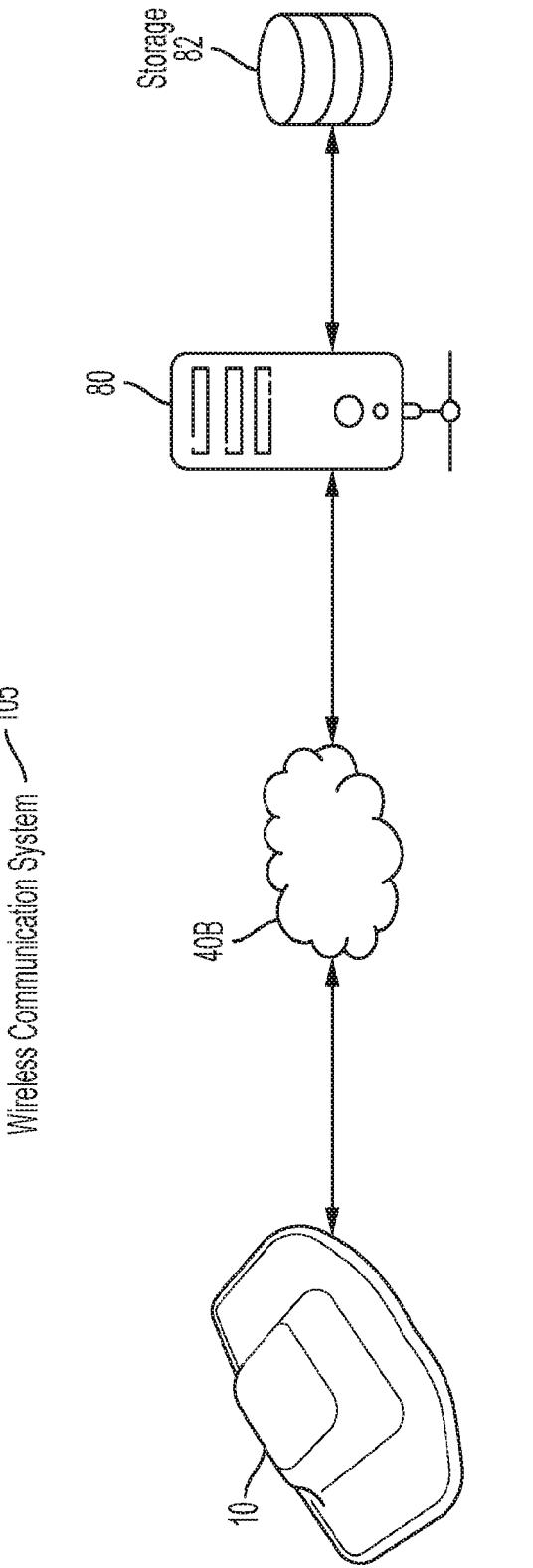
FIG. 19 is diagram of an exemplary wireless communication system, according to an embodiment having a Wireless Wide-Area Network (WWAN)

FIG. 19 is a diagram of a wireless communication system 105 having a sensor 10 connected to a WWAN 40B. The system 105 further includes operational equipment 30 in the form of a remote processor 80 in this embodiment. The remote processor 80 may be configured to receive and analyze the data and events via signal processing, filtering and data analysis, and event detection processes. In some embodiments, the remote processor 80 may store the data and events in a storage device 82. In an additional embodiment, the remote processor 80 may send information (e.g. alerts, patient status) determined based on the received data and analysis to another network, such as another wide area network or any network 40 (e.g. internet, cloud, cellular system). In yet another embodiment, the remote processor 80 can send control information determined based on the received data and analysis to the sensor 10 via the WWAN 40B. There may be a plurality of sensors 10 in the system worn by a single patient or by multiple patients in one or more locations.

The wireless communication system 105 having WWAN 40B may provide additional functionality to the disclosed embodiments by enabling transmission of sensor data over cellular networks, for example. As described herein, compatibility of technology is a challenge to bringing together various components in a medical monitoring system. Previous embodiments describe a connection adapter 20 that enable wireless communication with monitoring equipment, a wireless cellular transceiver is an embodiment of a connection adapter that enables sensor communication with the WWAN 40B. In this way, operational equipment 30, such as a remote processor 80 may retrieve the sensor data through a similar connection to the WWAN 40B. This arrangement addresses the additional compatibility issues that may arise in situations such as those in which local networks such as Bluetooth and Wi-Fi are unavailable, but cellular networks (e.g., 5G, LTE) are in range. Moreover, the WWAN 40B broadens the connectivity range of sensor data and enables alerting and other messaging functionality across larger distances, such as between a patient at home and medical personnel at a hospital or other emergency service location.

However, it is often desirable to minimize transmission over WWANs. Wireless transmissions, especially on a wide area network, can negatively impact battery life of the transmitting device. In order to provide practical use of sensors 10 in wireless communication with WWAN 40B, various battery-saving techniques may be implemented. To extend battery life it is desirable to reduce the number of transmissions required and/or the quantity of data sent. To reduce the number of transmissions and/or the quantity of data sent, the sensor 10 can process, filter, and/or perform event detection on the sensor signal data. Sensor data filtering can eliminate sending redundant information or information that is not useful. In some embodiments the sensor 10 can evaluate the sensor data, detect events, and send only the event information to the remote processor 80. Sending only the event information and not the raw sensor information can reduce the amount of data sent and/or number of wireless transmissions. In some embodiments it may be desirable to only perform this evaluative data processing step of signal processing, filtering, data analysis, and event detection at the remote processor 80. Performing this step at the remote processor 80 can reduce the computing and battery life requirements for the sensor 10, thereby reducing cost, reducing component size, and extending battery life.

In yet another embodiment, the sensor and/or event data can be stored by the sensor 10 and sent as a "batch" to the remote processor 80. In batch mode, the sensor 10 can turn off the WWAN wireless circuitry (e.g., in an embodiment of the communications unit 16 having cellular data communication components) between transmissions, thereby saving battery power. Reducing the frequency of having to turn on the wireless circuitry of the sensor 10 can extend battery life by reducing the overhead of connecting to the WWAN 40B each time a small amount of data is sent. In a further embodiment, the remote processor 80 may store sensor and/or event data from the sensor 10 in storage device 82. Storing data and events allows for trending and historical analysis, for example. In some embodiments, full data transmission from the sensor 10 may occur only in instances when the sensor 10 is actively charging—further improving battery life. In other embodiments, the onboard analytics of the sensor 10 may detect instances of high signal noise or poor skin adhesion. This can be achieved in instances where the sensor detects a poor skin adhesion via a lead off state. This may trigger the sensor 10 to stop data collection or reduce sampling rate to preserve battery power. The sensor 10 may also be toggled from various modes of operation via gestures (e.g. shaking the sensor) sensed by the onboard accelerometer or via a mechanical button embedded in the sensor.

Figure 20:
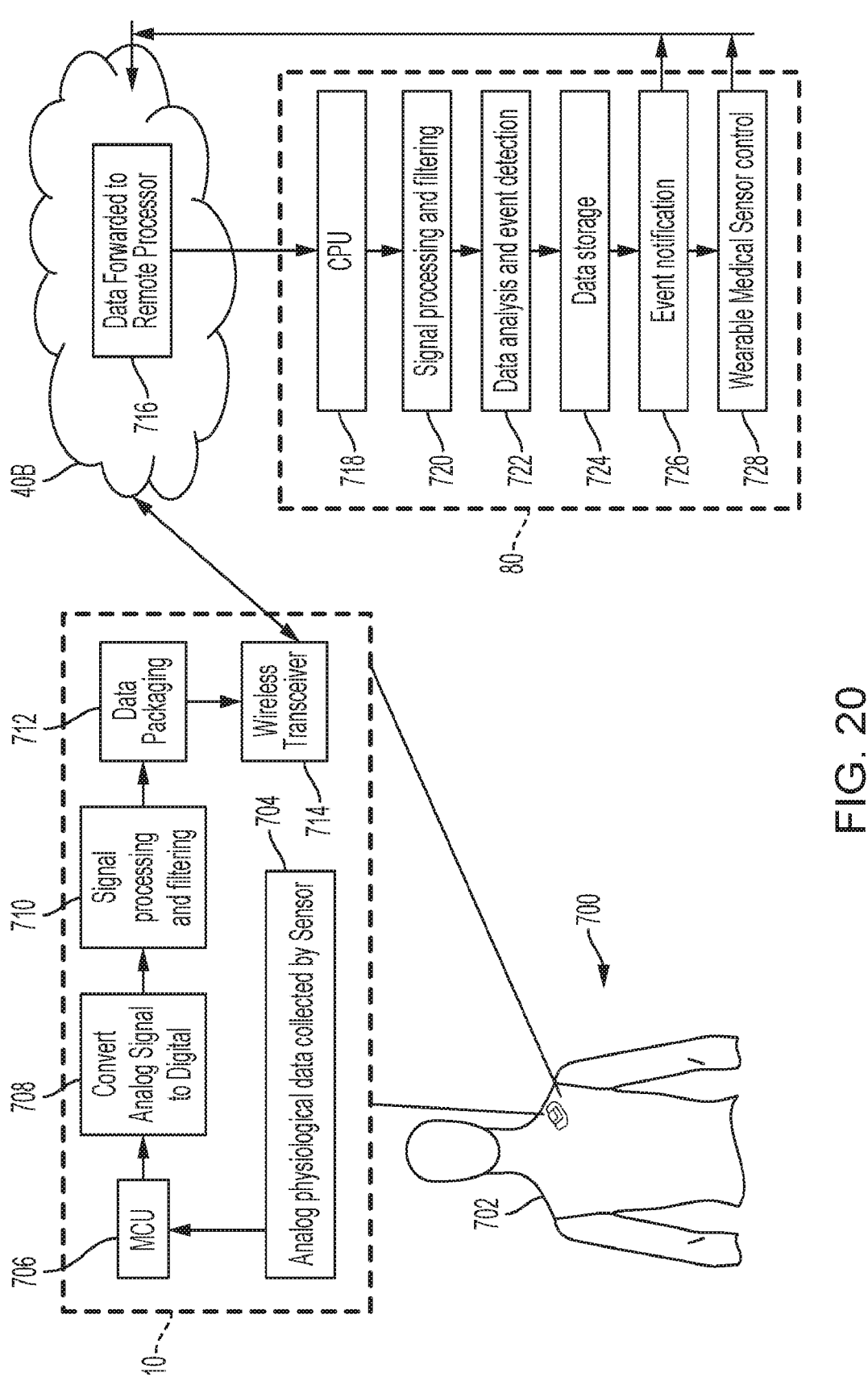
FIG. 20 is a flowchart of an exemplary process for distributing data from a sensor via the WWAN.

FIG. 20 is a flowchart of a process 700 for wireless event notification based on sensor data from a sensor 10 connected to WWAN 40B. In some embodiments, the sensor 10 sends either raw sensor data or event information derived from analysis of the sensor data via the WWAN 40B to the remote processor 80. In one embodiment the remote processor 80 can be configured to recognize critical events (e.g. irregular heart rhythm or low blood oxygen) or combinations of related events (e.g. both respiration and heart rate are elevated), and the remote processor 80 can send an event notification to appropriate personnel or medical devices or systems.

In step 702, the sensor 10 is positioned for collecting data, such as through placement on a user for physiological data collection and collects such data in step 704. In step At step 706, the MCU 12 receives the analog data. At step 708, the A/D converter 14 converts the processed analog signal into a digital signal. At step 710 the MCU 12 processes and filters the data according to processing functions stored in a memory connected to the MCU 12. At step 712 the MCU 12 packages the converted signal for transmission. At step 714, the communications unit 16, such as a wireless cellular transceiver, provides the packaged data to the WWAN 40B for wireless transmission. The transmission is forwarded through the WWAN 40B to the remote processor 80 at step 716.

In step 718, the remote processor 80 receives the sensor data at a CPU and performs signal processing and filter at step 720, data analysis and event detection at step 722, and data storage at step 724. In this way, the remote processor 80 may receive sensor data and analyze the data for various functions, such as alerting to events, storing for comprehensive analysis, forwarding to other operational equipment 30 for display, etc. In step 726, the remote processor 80 may perform event notification, such as by delivering data back to the WWAN 40B for communication with a remote device. In step 728, the remote processor is configured to perform sensor feedback control by providing control instructions back to the sensor 10 through the WWAN 40B.

Figure 21:
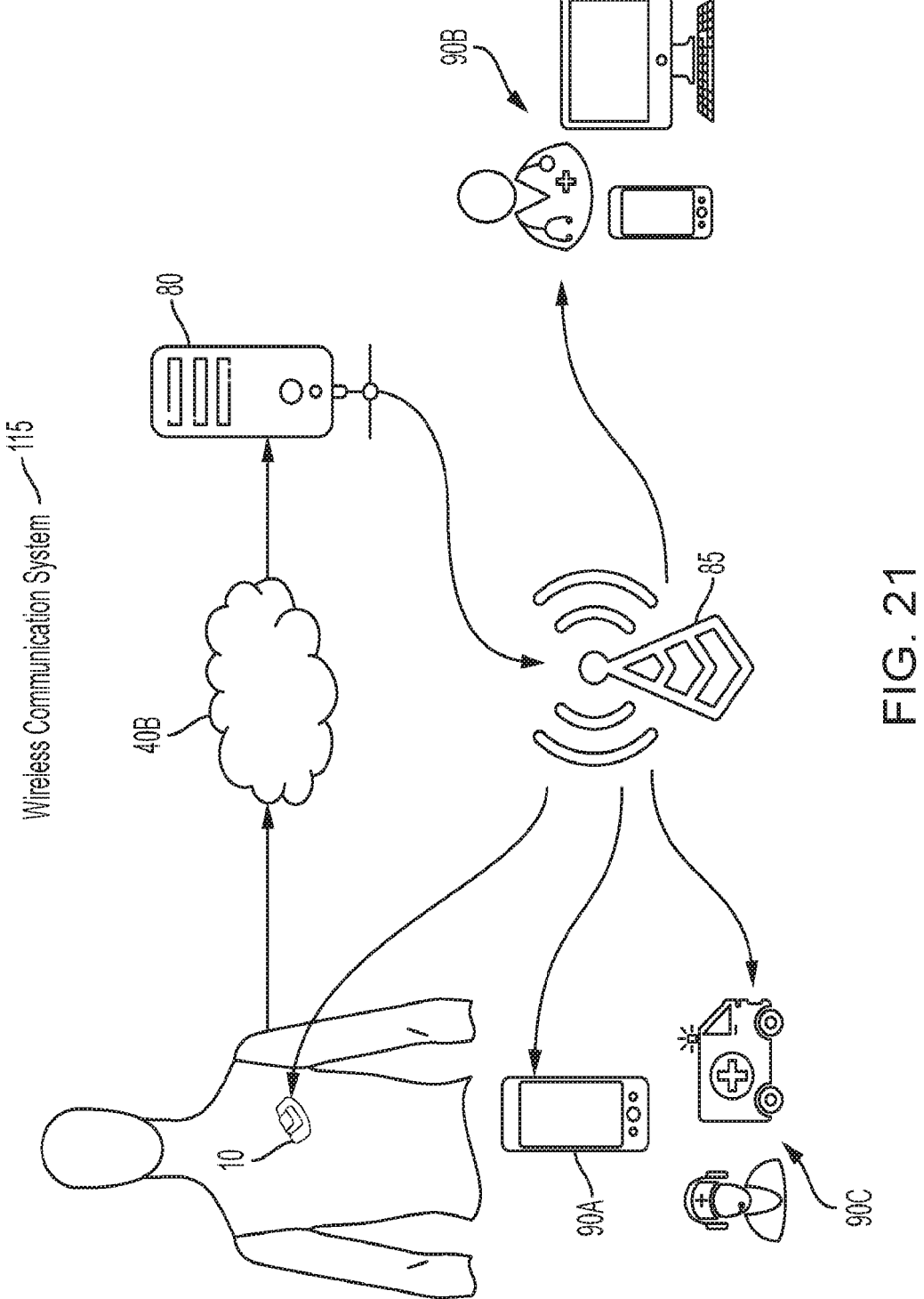
FIG. 21 is a diagram of the wireless communication system, according to an embodiment including a local node in communication with the WWAN.

FIG. 21 is a diagram of a wireless communication system 115 having the WWAN 40B, and, in some embodiments, a Wide-Area Network (WAN) 85 in communication with the remote processor 80 and at least one sensor 10. In some embodiments, the components of the system 115 may enable one or more functions described in the process 700 of FIG. 20, such as event alerting and/or sensor control.

The WAN 85 may be, for example, the Internet, a cloud solution, or a cellular network. In some examples, the WAN 85 is a different network from the WWAN 40B. In other embodiments, the WAN 85 is part of the WWAN 40B. In the system 115, the remote processor 80 is configured to receive notification of a detected event and provide information over the WAN 85 to another device, such as a device 90A, 90B, 90C or back to the sensor 10 itself to provide a warning to the wearer of the sensor 10. For example, a critical event that is processed in the remote processor 80 can be sent back to the sensor 10 and will alert the critical event to the wearer through a haptic feedback, a visual notification(LED), or a sound notification.

The device 90A may be a device, such as a mobile device (e.g., smartphone, tablet, etc.), associated with a user as another path for delivering an event detection notification to the wearer of the sensor 10 or another relevant user. In another embodiment, the event notification may be sent to another piece of medical equipment 90B (e.g. a standard medical monitor) or another medical system. In an additional embodiment, the critical event along with a location captured by a GPS device in the sensor 10 may be sent to an emergency response system device 90C.

Figure 22:
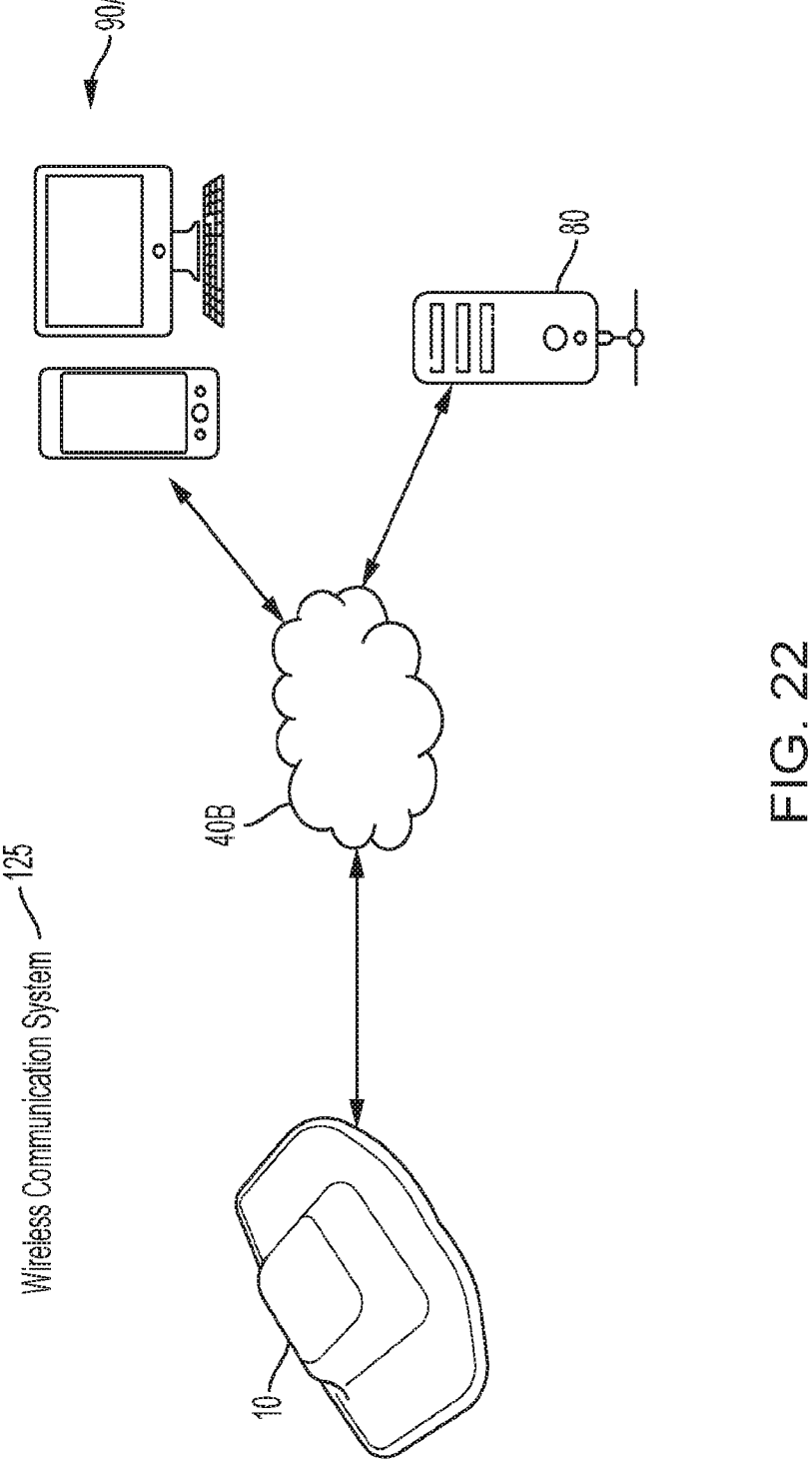
FIG. 22 is a diagram of the wireless communication system, according to an embodiment having multiple devices connected to the WWAN.

FIG. 22 is a diagram of a wireless communication system 125 further describing feedback control of a sensor 10 through connection of the remote processor 80 and, in some embodiments, a device 90A to the WWAN 40B. The sensor 10 sends either raw sensor data or event information derived from analysis of the sensor data via the WWAN 40B to the remote processor 80. In one embodiment the remote processor 80 is configured to recognize critical events (e.g. irregular heart rhythm or low blood oxygen) or combinations of related events (e.g. both respiration and heart rate are elevated), and the remote processor 80 can determine an appropriate control operation to perform on the sensor 10 (e.g. turn on a microfluidic pump, enable or disable various sensors). The remote processor 80 is configured to send the control information to the sensor 10 over the WWAN 40B. In an anther embodiment, a sensor interface application at the device 90BA may be used to send control operations to the sensor 10 over the WWAN 40B based on a modality desired by the healthcare provider or the wearer of the sensor 10, for example.

Figure 23:
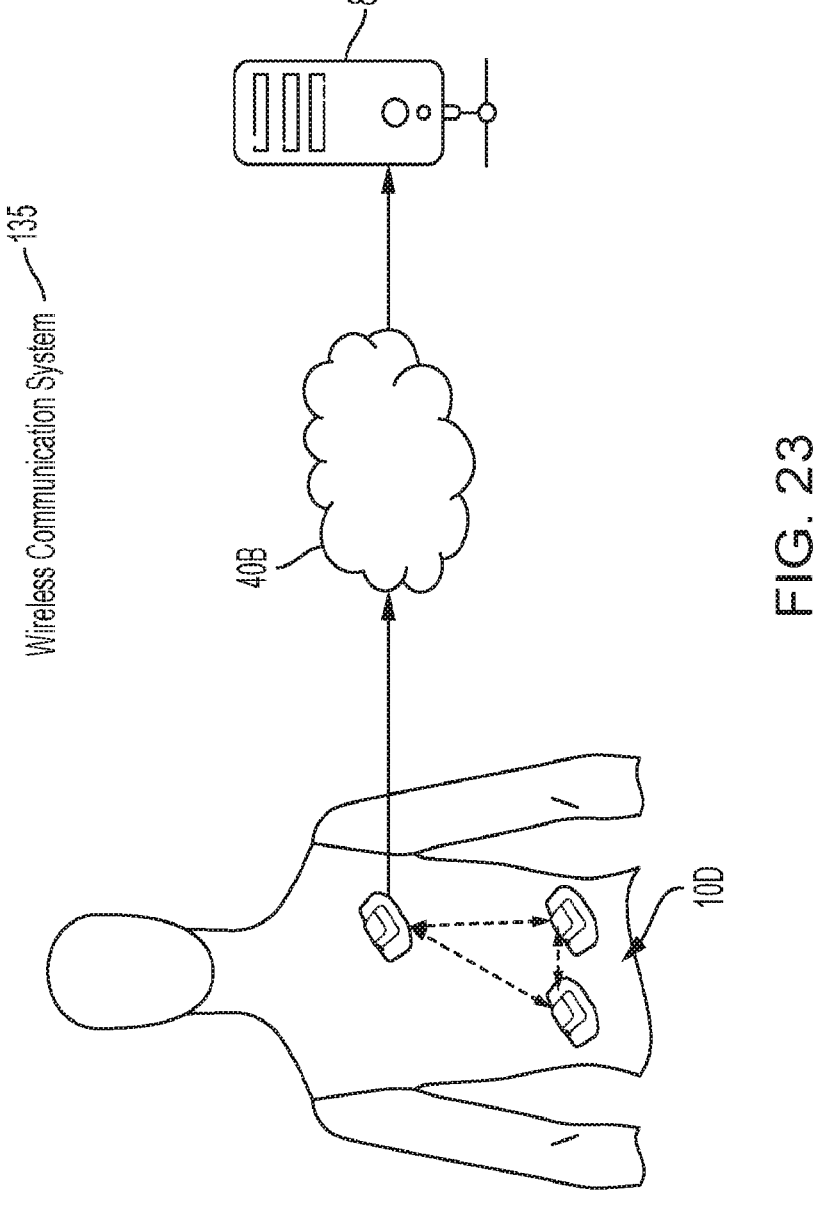
FIG. 23 is a diagram of the wireless communication system, according to an embodiment having multiple sensors connected to the WWAN.

FIG. 23 is a diagram of a wireless communication system 135 having a network of sensors 10D connected to the WWAN 40B. The sensors 10D may be connected to each other (e.g., via network 40) and configured to collect various medical data streams. For example, the sensors 10D may implement different sensors and/or be located on different parts of the body in order to serve different purposes (e.g. monitoring heart rate on the chest, monitoring skin temperature on a limb). The plurality of sensors 10D may function independently or may act in a coordinated fashion. Sensors 10D that act together may communicate between each other using a local area network (LAN) or personal area network (PAN) (e.g. Bluetooth, Zigbee). In one embodiment, sensors 10D may have different communication capabilities where, for example, one of the devices is a gateway device and has WWAN capabilities and the others do not. The gateway device may have higher battery capacity, for example. Sensors without WWAN capability may coordinate and send their data and events to the gateway device for transmission on the WWAN 40B to the remote processor 80. In another embodiment, all sensors 10D have the same WWAN capabilities, but they elect one of the sensors 10D to service as the gateway device. The step of electing a gateway can be performed, for example, by evaluating a number of criteria such as the processing or battery capabilities of the sensors 10D or by determining which sensor has the best WWAN signal strength. Bidirectional communication between the WWAN and sensors 10D also allows for remote memory wiping from the sensors 10D when a data packet is fully received.

Figure 24:
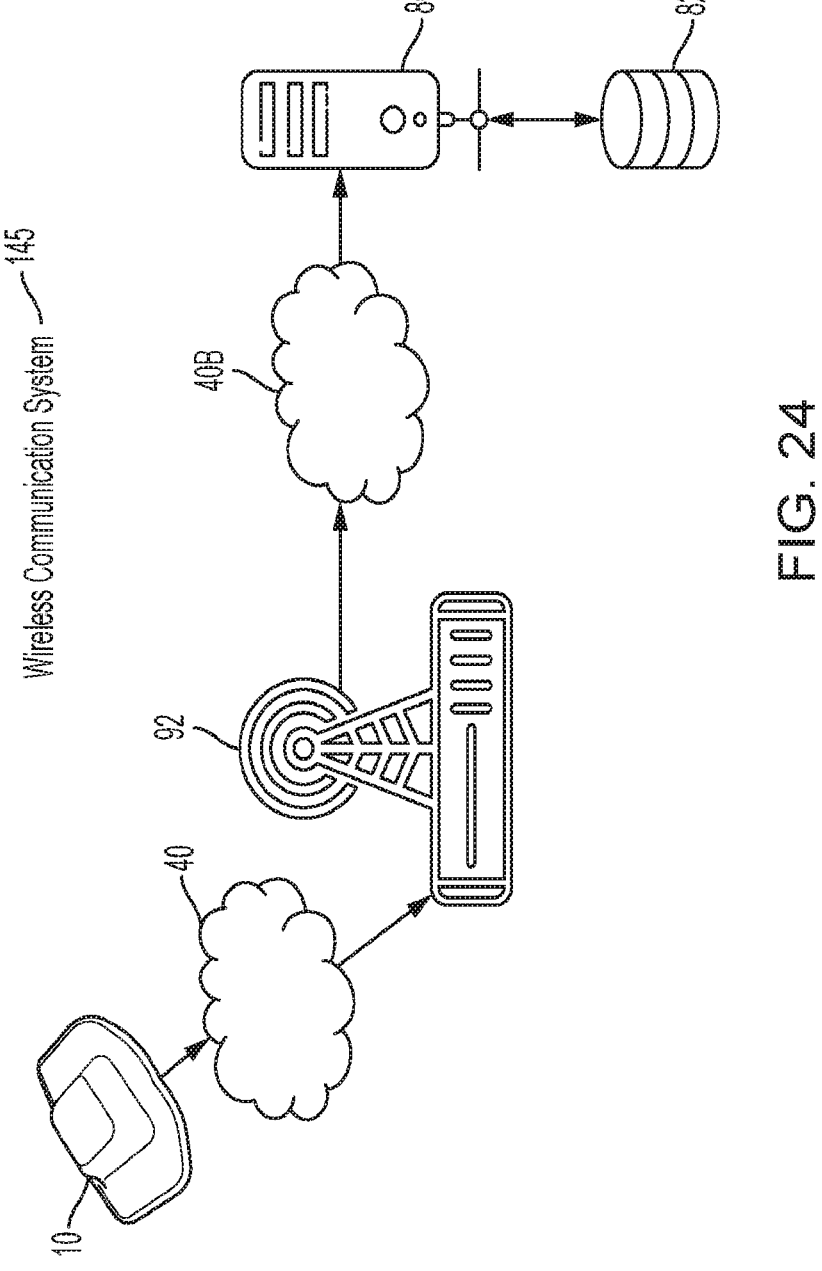
FIG. 24 is a diagram of the wireless communication system, according to an embodiment having a WWAN-capable base station.

FIG. 24 is a diagram of a wireless communication system 145 having a wireless base station 92 in communication with the sensor 10 and the WWAN 40B. In an embodiment, the sensor 10 is configured to apply signal processing, filtering, and triggers event detection and then transmits data and events to the base station 92 through network 40 (e.g., Bluetooth, Wi-Fi, LAN, etc.). In this way, the base station 92 may act as the connection adapter 20 for connecting the sensor to operational equipment, such as the remote processor 80 via WWAN 40B. The base station 92 may have at least two different network communication units, such as Bluetooth capability for connection to network 40 and cellular data capability for connection to WWAN 40B. In other embodiments, the base station has only WWAN functionality and communicates with sensor 10 and remote processor 80 over WWAN 40B (e.g., network 40 and WWAN 40B are the same network).

In some embodiments, the base station 92 may perform signal processing, filter, and event detection. The base station 92 is configured to transmit data (e.g., raw data, packaged data, events detected by the sensor and/or the base station, etc.) over the WWAN 40B to the remote processor 80. The remote processor 80 is configured to receive and analyze the data and events via signal processing, filtering, data analysis, and event detection (48). In some embodiments, the remote processor 80 may store the sensor data (e.g., analyzed data, detected events, etc.) in the storage device 82.

Figure 25:
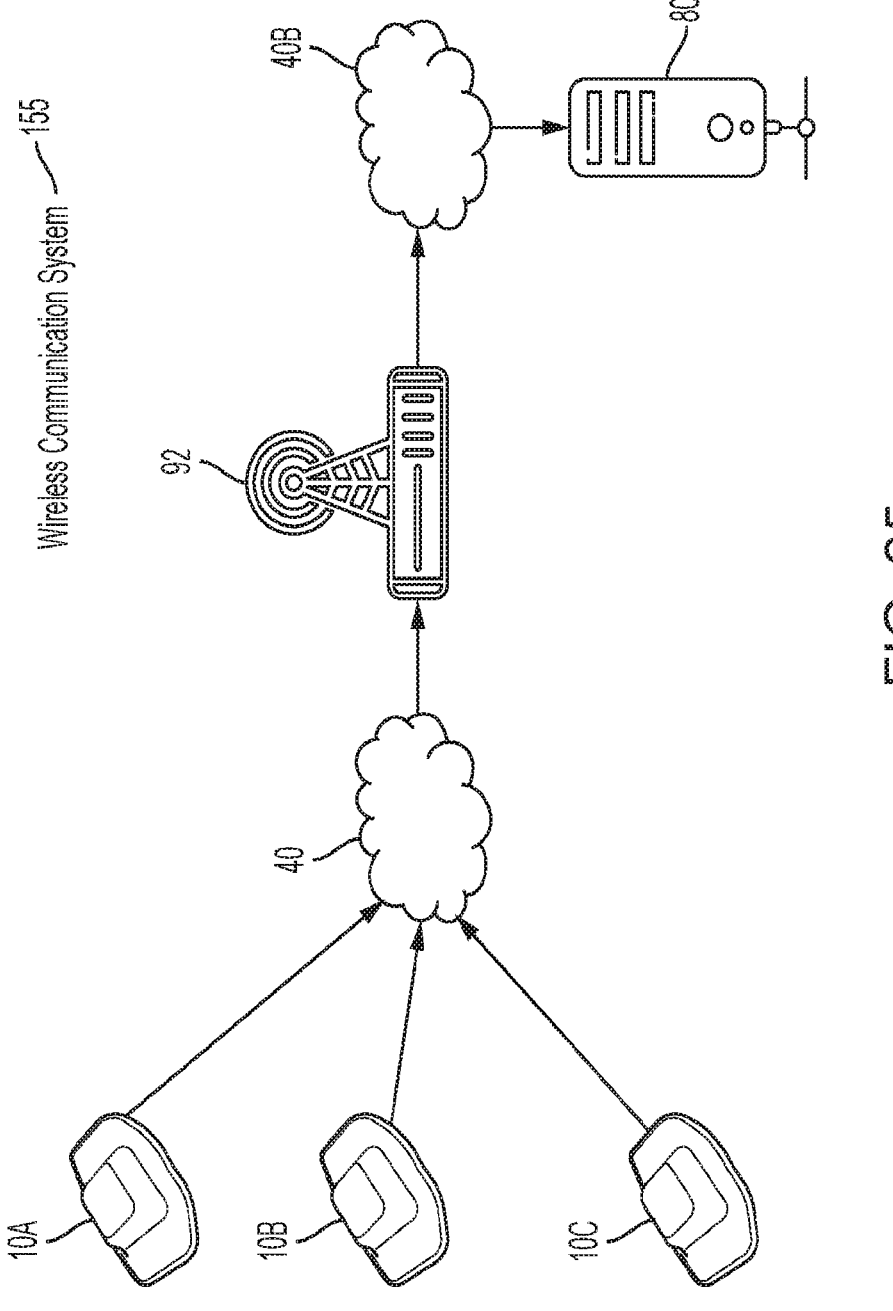
FIG. 25 is a diagram of the wireless communication system, according to an embodiment having the WWAN-capable base station and multiple sensors in communication therewith.

FIG. 25 is a diagram of a wireless communication system 155 in which multiple sensors 10A, 10B, 10C are connected to the base station 92 by the network 40 (e.g., Bluetooth, Wi-Fi, LAN, etc.). The base station 92 may, for example, have multiple Bluetooth radios to allow high bandwidth of data to be consumed from the multiple sensors 10. The base station 92 may apply signal processing, filtering, and data analysis, and event detection for one or more of the sensors 10A, 10B, 10C. The base station 92 is configured to send data from the sensors 10A, 10B, 10C to the remote processor 80 via the WWAN 40B.

Figure 26:
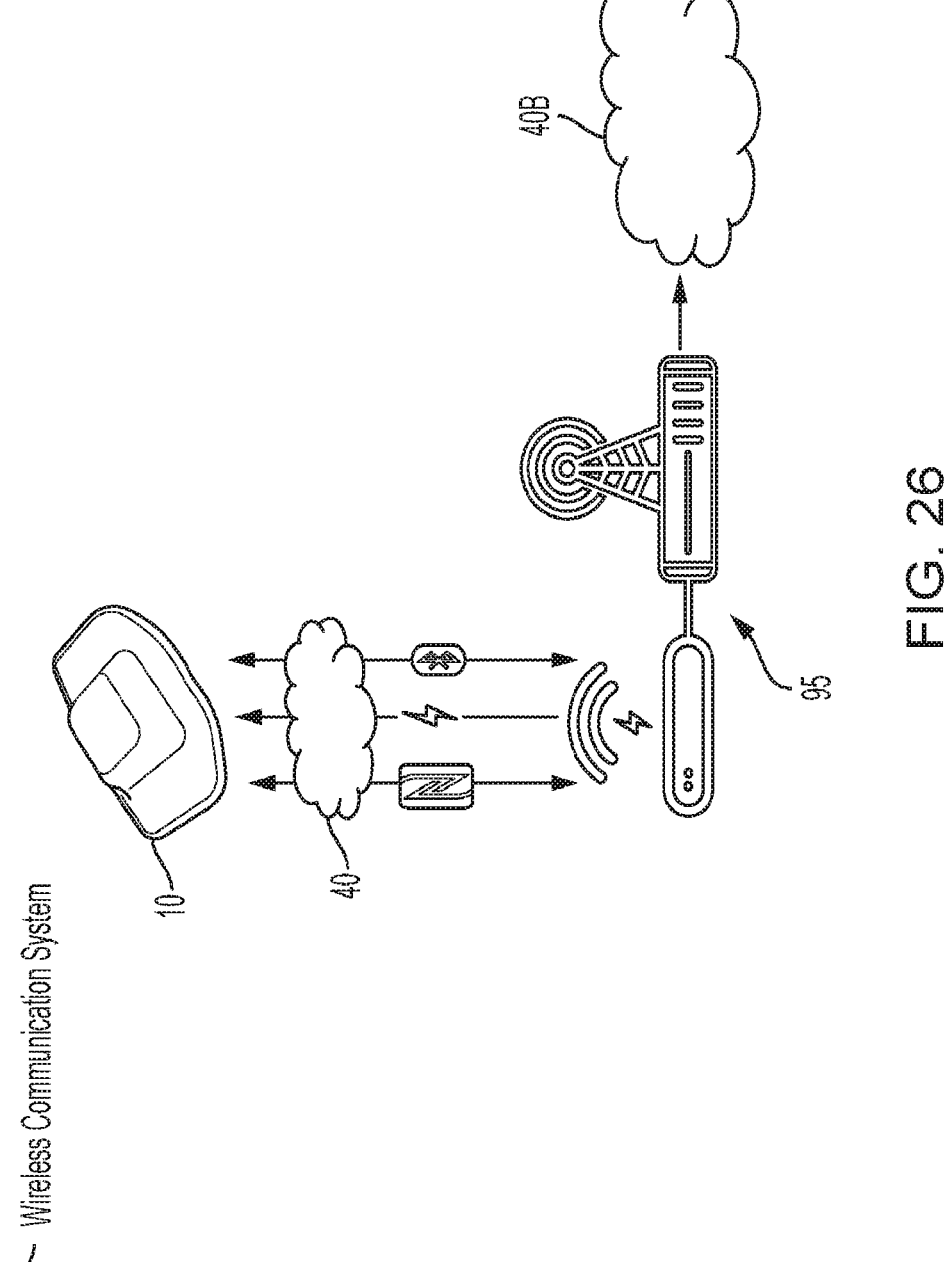
FIG. 26 is a diagram of the wireless communication system, according to an embodiment having a wireless charger for a sensor configured to communicate with the WWAN.
Figure 27:
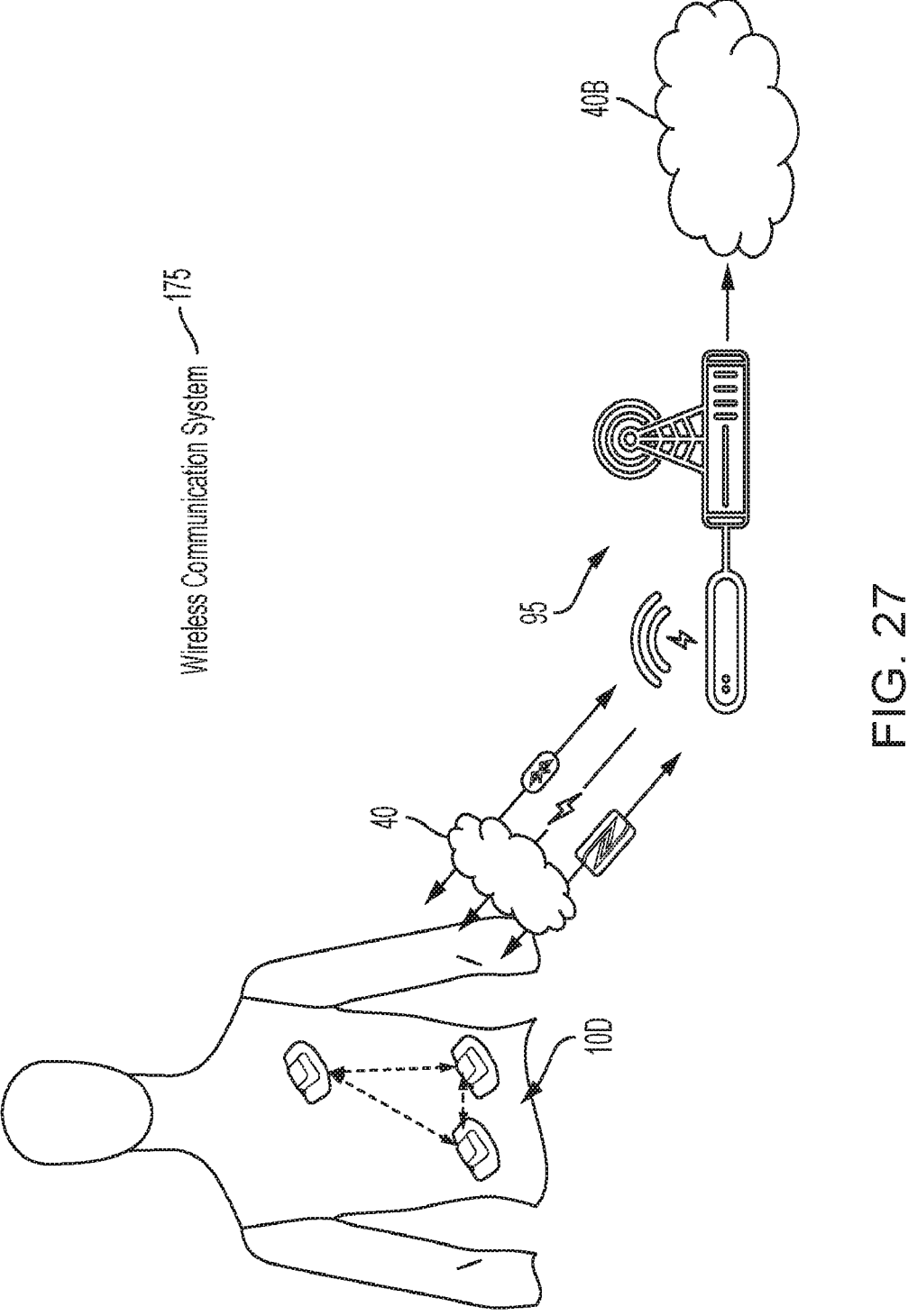
FIG. 27 is a diagram of the wireless communication system, according to an embodiment having the wireless charger and multiple sensors in communication therewith.

FIG. 26 is a diagram of a wireless communication system 165 having a connection adapter in the form of a charging station 95. The charging station 95 enables sensor communication with the WWAN 40B and provides additional functionality such as wireless charging and sensor authentication. The sensor 10 may authenticate to the charging station 95 using NFC for secure network communication over network 40. The sensor 10 may also transmit data while it is placed on the charging station 95 for a stable power source while transmitting large amounts of data. The charging station 95 may analyze data and events via signal processing, filtering, data analysis, and event detection. The charging station 95 may also include cellular networking capabilities to transmit the data to the WWAN 40B. FIG. 27 is a diagram of a similar wireless communications system 175 in which a network of sensors 10D are connected to the charging station 95. The sensors 10D may include a local/personal area network (e.g., using Bluetooth). Data is transmitted from the sensors 10D to the charging station 95 via the network 40. In some embodiments, a gateway in communication with the sensors 10D may be placed on the charging station 95 and simultaneously receive electrical charge while also forwarding data from the sensors 10D to a transceiver portion of the charging station 95 with connectivity to the WWAN 40B. The charging station 95 may apply signal processing, filtering, data analysis, and event detection and forward as sensor data to the WWAN 40B.

The disclosed embodiments are applicable to data networking systems in which data collection and transmission occurs, such as in medical patient monitoring applications. The disclosed embodiments of a wireless communication system provide additional functionality to wireless sensors, such as soft, flexible, wearable sensors worn by medical patients for detecting signals indicative of parameters such as patient vital signs. The disclosed wireless communication systems, in at least some embodiments, provide a connection adapter for providing at least some of the communications functionality described herein. The disclosed connection adapters generally provide communication functionality that enables sensor data to be transmitted to operational equipment such as patient monitors, personal devices, emergency service devices, remote processors, etc. As disclosed herein, a connection adapter may be, for example, a separate hardware dongle for direct connection to a monitoring system to enable the monitoring system to receive wireless communication that it may not otherwise be capable of receiving. This enables newer technology associated with wireless sensors, in large quantities, to be quickly and easily deployed in existing medical environments. In some other embodiments, connection adapters may be embedded hardware components build into operational equipment, or may be a virtual adapter in the form of software creating connectivity.

Disclosed embodiments also provide wireless communication systems for connecting wireless sensors to Wireless Wide-Area Networks, such as cellular data networks including 4G/LTE/5G, for example. A connection adapter may include a wireless transceiver at the sensor or operational equipment. In other embodiments, a connection adapter may be a base station or charging station for collection of sensor data over a connected local network and transmission of the data over the WWAN.

Wireless capability in medical sensor systems helps to overcome challenges in device compatibility, ease of use and deployment, and providing comprehensive care to multiple patients in a single environment or to a single patient with multiple sensors for vital sign monitoring. The disclosed embodiments help to provide this connectivity and compatibility without requiring major component upgrades or changes and, further, provides functionality across several different wireless networking options to meet the needs of a particular situation. Further, the disclosed embodiments provide authentication and security functionality for enabling high confidence in deploying the associated communication systems in a medical environment.

Disclosed embodiments provide various solutions for receiving and delivering wireless sensor data such that operational equipment can easily identify and use the sensor data as appropriate. Wireless sensors can be quicker and simpler to deploy to patients, avoiding the need for wire routing, enabling wearing on various points of the body without worrying about wire placement, but which may face challenges in the current state of technology in communicating with all of the various devices that use the sensor data. The disclosed embodiments provide connection adapters that cause the operational equipment to receive the sensor data and which include a hardware or software key for enabling the operational equipment to quickly, easily, and securely identify the sensor data it is receiving. These features help to save time, a vital asset in a medical environment, and cost through connecting existing equipment avoiding requiring expensive upgrades simply to allow devices to communicate with each other.

This disclosure is not limited to the particular systems, devices and methods described, as these may vary. The terminology used in the description is for the purpose of describing the particular versions or embodiments only, and is not intended to limit the scope.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A wireless communication system, comprising:
a first network;
at least one sensor to detect a signal indicative of a parameter and generate sensor data therefrom and to transmit the sensor data wirelessly to the first network;
operational equipment comprising an operational-equipment processor incompatible with the wirelessly transmitted sensor data
the operational equipment further including:
an embedded data receiver integrally formed therein,
the embedded data receiver including at least a wireless communication unit and a microcontroller unit for receiving and processing sensor data received from the first network, and
the embedded data receiver further comprising a software application having a virtual software key, the software application installed therein so as to teach the embedded data receiver to communicate with the at least one sensor to identify the wirelessly transmitted sensor data as from a trusted source,
the embedded data receiver further configured to wirelessly receive the wirelessly transmitted sensor data from the trusted source via the first network, and to reconstruct the wirelessly transmitted sensor data into a form compatible with the operational-equipment processor.

2. The wireless communication system of claim 1, wherein the at least one sensor comprises a microcontroller unit and an analog-to-digital converter.

3. The wireless communication system of claim 1, wherein the operational equipment comprises a patient monitor, and wherein the operational equipment further comprises at least one output device for displaying the reconstructed sensor data.

4. The wireless communication system of claim 1, wherein the at least one sensor is a wearable sensor and the parameter is a vital sign.

5. The wireless communication system of claim 4, wherein the at least one sensor is flexible and/or stretchable.

6. The wireless communication system of claim 1, wherein:

the operational equipment is communicatively coupled to a separate alarming system; and the separate alarming system includes a separate embedded data receiver therein for analyzing monitored data and providing feedback to the at least one sensor through the first network.

7. A wireless communication system, comprising:

a first network;

at least one sensor to detect a signal indicative of a parameter and generate sensor data therefrom and to transmit the generated sensor data wirelessly to the first network;

operational equipment comprising an operational-equipment processor incompatible with the wirelessly transmitted sensor data;

the operational equipment further including:

an embedded data receiver integrally formed therein and configured to process the sensor data generated by the at least one sensor that is received wirelessly by the embedded data receiver from the first network, and further configured to identify the generated sensor data received from the first network as being from a trusted source so as to reconstruct the generated sensor data into a form compatible with the operational-equipment processor.

8. The wireless communication system of claim 7, wherein the embedded data receiver is further configured to accept the wirelessly transmitted sensor data generated from the at least one sensor and to wirelessly transmit data to the at least one sensor for triggering actions of the at least one sensor through feedback control.

9. The wireless communication system of claim 8, wherein the triggered actions include visual actions, sound actions, and haptic notification actions of the at least one sensor.

10. The wireless communication system of claim 7, further comprising:

a separate alarming device communicatively coupled to the operational equipment and including a separate embedded data receiver therein for analyzing monitored data and providing feedback to the at least one sensor through the first network.

11. The wireless communication system of claim 7, wherein the embedded data receiver further includes an installed software application configured to teach the embedded data receiver to communicate with the at least one sensor so as to identify the generated sensor data received from the first network as being from a trusted source.

12. The wireless communication system of claim 7, wherein the embedded data receiver further includes a downloadable virtual software key installed therein to match the at least one sensor to the operational equipment so that the generated sensor data received from the first network is identified as being from a trusted source.

13. The wireless communication system of claim 7, wherein the embedded data receiver further includes:

a wireless communication unit for wirelessly receiving, via the first network, the sensor data generated by the at least one sensor via and wirelessly transmitted to the first network, and a microcontroller unit for performing data reconstruction, signal processing, and filtering of the received sensor data to deliver reconstructed sensor data from the generated sensor data into a form compatible with the operational-equipment processor for further processing and display.

14. The wireless communication system of claim 13, wherein the operational equipment includes a patient monitor and at least one output device for displaying the reconstructed sensor data delivered by the microcontroller unit.

* * * * *